United States Patent
Mets

(10) Patent No.: US 12,416,025 B2
(45) Date of Patent: Sep. 16, 2025

(54) SYSTEM FOR THE PRODUCTION OF METHANE FROM $CO_2$

(71) Applicant: THE UNIVERSITY OF CHICAGO, Chicago, IL (US)

(72) Inventor: Laurens Mets, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 632 days.

(21) Appl. No.: 17/116,629

(22) Filed: Dec. 9, 2020

(65) Prior Publication Data

US 2021/0115477 A1  Apr. 22, 2021

Related U.S. Application Data

(63) Continuation of application No. 15/647,539, filed on Jul. 12, 2017, now abandoned, which is a continuation of application No. 14/480,534, filed on Sep. 8, 2014, now abandoned, which is a continuation of application No. 12/333,932, filed on Dec. 12, 2008, now abandoned, which is a continuation-in-part of application No. PCT/US2007/071138, filed on Jun. 13, 2007.

(60) Provisional application No. 61/028,413, filed on Feb. 13, 2008, provisional application No. 60/813,020, filed on Jun. 13, 2006.

(51) Int. Cl.
*C12P 5/02* (2006.01)
*C12M 1/00* (2006.01)
*C12M 1/107* (2006.01)

(52) U.S. Cl.
CPC ............. *C12P 5/023* (2013.01); *C12M 21/04* (2013.01); *C12M 29/24* (2013.01); *C12M 43/04* (2013.01); *C12M 45/06* (2013.01); *C12M 47/18* (2013.01); *Y02E 50/30* (2013.01)

(58) Field of Classification Search
CPC ................................................ C12P 5/02–023
See application file for complete search history.

(56) References Cited

U.S. PATENT DOCUMENTS

| | | | |
|---|---|---|---|
| 1,940,944 A | 12/1933 | Fischer et al. | |
| 2,097,454 A | 11/1937 | Fischer et al. | |
| 3,640,846 A | 2/1972 | Johnson | |
| 3,981,800 A | 9/1976 | Ort | |
| 4,022,665 A | 5/1977 | Ghosh et al. | |
| 4,540,666 A | 9/1985 | Nukina et al. | |
| 4,620,928 A | 11/1986 | Gott | |
| 4,722,741 A | 2/1988 | Hayes et al. | |
| 4,883,753 A | 11/1989 | Belaich et al. | |
| 4,921,799 A | 5/1990 | Kitaura et al. | |
| 5,143,835 A | 9/1992 | Nakatsugawa et al. | |
| 6,340,581 B1 | 1/2002 | Gaddy | |
| 6,663,777 B2 | 12/2003 | Schimel | |
| 6,667,171 B2 | 12/2003 | Bayless et al. | |
| 6,716,351 B2 | 4/2004 | Fassbender | |
| 6,802,974 B2 | 10/2004 | Rebholz et al. | |
| 7,033,822 B2 | 4/2006 | Maston | |
| 9,428,745 B2 | 8/2016 | Mets | |
| 2003/0175942 A1 | 9/2003 | Kim et al. | |
| 2009/0130734 A1 | 5/2009 | Mets | |
| 2009/0317882 A1 | 12/2009 | Cheng et al. | |
| 2011/0165667 A1 | 7/2011 | Mets | |
| 2011/0287504 A1 | 11/2011 | Mets | |
| 2014/0377830 A1 | 12/2014 | Mets | |
| 2016/0319305 A1 | 11/2016 | Mets | |
| 2018/0094283 A1 | 4/2018 | Mets | |
| 2018/0208884 A1 | 7/2018 | Mets | |

FOREIGN PATENT DOCUMENTS

| | | | | |
|---|---|---|---|---|
| DE | 3230197 | * | 8/1982 | ............. C12P 5/023 |
| DE | 10330375 A1 | | 12/2004 | |
| EP | 0253744 A1 | | 1/1988 | |
| EP | 1574581 A2 | | 9/2005 | |
| JP | 62236489 A | | 10/1987 | |
| WO | WO-2006108532 A1 | * | 10/2006 | ............. B01D 53/62 |
| WO | WO-2007014717 A1 | * | 2/2007 | ................ C02F 3/28 |
| WO | WO-2008/094282 A1 | | 8/2008 | |

OTHER PUBLICATIONS

Roger A. Garrett, "Genomes: Methanococcus jannaschii and the golden fleece" Current Biology 1996, vol. 6 No 11:1377-1380 (Year: 1996).*

Nicks et al. "Fossil-fueled power plants as a source of atmospheric carbon monoxide" J. Environ. Monit., 2003, 5, 35-39 (Year: 2003).*

Song et al. "Tri-reforming of Methane over Ni Catalysts for CO2 Conversion to Syngas With Desired H2/CO Ratios Using Flue Gas of Power Plants Without CO2 Separation" Studies in Surface Science and Catalysis 153, 2004, pp. 315-322 (Year: 2004).*

Tsao et al. "Continuous Culture of Methanococcus jannaschii, an Extremely Thermophilic Methanogen" Biotechnology and Bioengineering, vol. 43, pp. 258-261 (1994) (Year: 1994).*

MicrobeWiki "Methanococcus jannaschii" accessed at "https://microbewiki.kenyon.edu/index.php?title=Methanococcus_jannaschii&oldid=64912", 7 pages edited on Jul. 1, 2011 (Year: 2011).*

Air Dispersion Modeling Conversion and Formula Reference (archived Jun. 10, 2004; website accessed at <https://web.archive.org/web/20040610205839/http://www.air-dispersion.com/formulas.html)>.

Banchuen, T. ("Oxidation-Reduction (Redox) Reactions and Potentials," Master of Science Thesis Defense accessed by <http://scholar.lib.vt.edu/theses/available/etd-01102003-162857/:> 2002).

Baughn, A.D. et al., "The strict anaerobe bacteroides fragilis grows in and benefits from anomolar concentrations of oxygen," Nature (2004) 427:441-444.

(Continued)

*Primary Examiner* — Thane Underdahl

(74) *Attorney, Agent, or Firm* — MARSHALL, GERSTEIN & BORUN LLP

(57) ABSTRACT

A method of converting $CO_2$ gas produced during industrial processes comprising contacting methanogenic archaea with the $CO_2$ gas under suitable conditions to produce methane.

6 Claims, 16 Drawing Sheets

(56) References Cited

OTHER PUBLICATIONS

Brioukhanov et al., The catalase and superoxide dismutase genes are transcriptionally up-regulated upon oxidative stress in the strictly anaerobic archaeon Methanosarcina barkeri, Microbiology, 152(Pt 6):1671-7 (2006).

Bryant et al., "Methanobacillus omelianskii, a symbiotic association of two species of bacteria," Archiv. Microbiol. (1967) 59:20-31.

Call et al., Hydrogen production in single chamber microbial electrolysis cell lacking a membrane, Environ. Sci. Technol., 42:3401-6 (2008).

Daniel G. Villarroel Camacho, The Geochemistry of Silica in Icelandic Geothermal Systems, Faculty of Earth Sciences, University of Iceland (Sep. 2017).

De Poorter et al., Hydrogen concentrations in methane-forming cells probed by the ratios of reduced and oxidized coenzyme F420, Microbiology, 151(Pt. 5):1697-705 (2005).

European Patent Application No. 07872663.5, Communication Pursuant to Article 94(3) EPC, dated Feb. 26, 2019.

European Patent Application No. 07872663.5, Communication Pursuant to Article 94(3) EPC, dated Jun. 21, 2019.

European Patent Application No. 07872663.5, Communication Pursuant to Article 94(3) EPC, dated Mar. 11, 2020.

European Patent Application No. 07872663.5, Communication Pursuant to Rule 114(2) EPC, dated Sep. 25, 2019.

European Patent Application No. 07872663.5, Reply to Third-Party Observations, dated Mar. 2, 2020.

Ferry, J.G., "Microbiological principles of methane formation from biomass," Food Engineering News (1985) 4 pages.

Fetzer, S. et al., "Effect of redox potential on methanogenesis by Methanosarcina barkeri," Arch. Microbiol. (1993) 160:108-113.

International Search Report and Written Opinion of Application No. PCT/US07/71138 dated Dec. 6, 2007 (7 pages).

Jarrell, Extreme oxygen sensitivity in methanogenic archaebacteria, BioScience, 35(5):298-302 (May 1985).

Kato, M.T. et al., "Anaerobe tolerance to oxygen and the potentials of anaerobic and aerobic cocultures for wastewater treatment," Braz. J. Chem. Eng. (1997) 14(4):1-19.

Lu et al., Hydrogen production with effluent from an ethanol-H2-coproducing fermentation reactor using a single-chamber microbial electrolysis cell, Biosens Bioelectron., 24:3055-60 (2009).

Mantzaris et al., Growth processes in a cascade of bioreactors: Mathematical models, AICHE J., 45(1):164-76 (1999).

Mukhopadhyay, B. et al., "Reactor-scale cultivation of the hyperthermophilic methanarchaeon methanococcus jannaschii to high cell densities," Appl. Environ. Microbiol. (1999) 65(11):5059-5065.

Nishimura, N. et al., "Cultivation of thermophilic methanogen KN-15 on H2-0O2 under pressurized conditions," J. Fermentation and Bioengineering (1992) 73(6):477-480.

Ohmura et al., Electrochemical regeneration of Fe(III) to support growth on anaerobic iron respiration, Appl. Environ. Microbiol., 68(1):405-7 (2002).

Reeburgh, Rates of biogeochemical processes in anoxic sediments, Annu Rev Earth Planet Sci., 11:269-98 (1983).

Schill, N. et al., "Continuous cultures limited by a gaseous substrate: development of a simple, unstructured mathematical model and experimental verification with methanobacterium thermoautotrophicum," Biotech. Bioeng. (1996) 51:645-658.

Seedorf, H. et al., "F420H2 oxidase (FprA) from methanobrevibacter arboriphilus, a coenzyme F420-dependent enzyme involved in 02 detoxification," Arch. Microbiol. (2004) 182:126-137.

Sehested, J. et al., "Methanation of CO over nickel: mechanism and kinetics at high H2/CO ratios," J. Phys. Chem. B (2005) 109:2432-2438.

Sipma, J. et al., "Microbial CO conversions with applications in synthesis gas purification and bio-desulfurization," Critical Reviews in Biotechnology (2006) 26:41-65.

Sowers, et al., "Techniques for Anaerobic Growth," Protocol 1, pp. 15-47.

Supplementary European Search Report for corresponding European application No. EP07872663, dated Jan. 9, 2012.

Torres et al., Selecting anode-respiring bacteria based on anode potential: phylogenetic, electrochemical, and microscopic characterization, Environ. Sci. Technol., 43:9519-24 (2009).

Vermeij et al., Purification and properties of coenzyme F390 hydrolase from Methanobacterium thermoautotrophicum (strain Marburg), Eur J Biochem. Dec. 1, 1995;234(2):592-7.

Wise, D.L et al., "Biomethanation: anaerobic fermentation of CO2, H2 and CO to methane," Biotech. Bioeng. (1978) XX:1153-1172.

Woese et al., "Towards a natural system of organisms: proposal for the domains Archaea, Bacteria, and Eucharya," Proc. Natl. Acad. Sci. USA (1990) 87(12):4576-4579.

Zehnder, A.J.B. et al., "Physiology of methanobacterium strain AZ," Arch. Microbiol. (1977) 111:199-205.

Zehnder, Ecology of methane formation, IN: Mitchell, Water Pollution Microbiology, 2nd ed., New York: John Wiley & Sons, pp. 349-376 (1976).

* cited by examiner

SYSTEM FOR THE PRODUCTION OF METHANE FROM CO$_2$

CROSS REFERENCE TO RELATED APPLICATIONS

This application is a continuation-in-part under 35 U.S.C. 1.111 of International Application No. PCT/US2007/071138, filed Jun. 13, 2007, which claims the benefit of priority to U. S. Provisional Application No. 60/813,020, filed Jun. 13, 2006. This application also claims the benefit of priority to U.S. Provisional Application No. 61/028,413, filed Feb. 13, 2008, all of which are incorporated herein by reference in their entirety.

BACKGROUND OF THE INVENTION

Energy self-sufficiency and sustainable energy systems with lower environmental impacts are critical national goals. Increased use of biomass-derived ethanol as a fuel is advantageous because it uses solar energy, rather than fossil fuel energy, as a portion of its energy input and CO$_2$ obtained by photosynthesis from the environment as a portion of its material requirement for energy carriers. At present ethanol production from corn requires significant energy input from fossil fuels for distillation of the final product and for drying of fermentation residues for use in animal feed. Present domestic ethanol production methods, therefore, are not energetically or economically competitive with ethanol produced abroad from sugar cane. In addition, one third of the carbon in the corn starch is released as a concentrated CO$_2$ stream during ethanol production. The U.S. Department of Energy has identified that increasing the energy efficiency and reducing the CO$_2$ emissions of the fuel ethanol production process is essential for increasing the role of ethanol in meeting our energy needs. Currently, fuel ethanol production relies on federal subsidies for its economic viability. Therefore, it will be important to achieve greater economic efficiency in the ethanol production process if the industry is to be viable and self-sustaining.

The present invention provides a system that reduces the CO$_2$ emissions from industrial processes, including ethanol production, by using a bioreactor system that uses the emissions to produce methane (natural gas).

SUMMARY OF THE INVENTION

The present invention provides a system that converts the CO$_2$ into methane (natural gas). The present invention utilizes CO$_2$ produced by industrial processes. Examples of processes that that produce CO$_2$ are biomass fermentation to produce liquid fuels and coal and biomass gasification processes. Gasification is a process that converts carbonaceous materials, such as coal, petroleum, petroleum coke or biomass (living or dead biological material), into carbon monoxide, hydrogen and carbon dioxide. In the system of the present invention, CO$_2$ industrial waste-gas streams, such as those formed during the production of ethanol or those produced by combined cycle coal fired energy plants, is combined with hydrogen and undergoes a microbial fermentation process catalyzed by methanogenic archaea, producing methane and water. Hydrogen gas may be produced from a variety of sources. In one embodiment, inexpensive electric power can be used to produce hydrogen from water via electrolysis. The integrated electrolysis/methane fermentation system can be viewed as converting an intermittent energy source (e.g. inexpensive off-peak electricity from power plants) to a stable chemical energy store, using hydrogen as an intermediate and methane as the final energy carrier.

The present invention uses a bioreactor containing methanogenic archaea to catalyze the following chemical reaction:

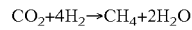

$$CO_2 + 4H_2 \rightarrow CH_4 + 2H_2O$$

This reaction occurs with high efficiency with >95% conversion of CO$_2$ to methane at moderate temperatures. Suitably the bioreactor conditions will allow a reaction vessel that is 1/10 or less the volume of the ethanol fermentation system to handle all of the CO$_2$ stream.

In one embodiment, the present invention provides a method of converting carbon dioxide produced during an industrial process to methane comprising contacting a culture comprising methanogenic archaea with H$_2$ gas and an output gas from an industrial process comprising CO$_2$ gas in a bioreactor under suitable conditions to produce methane. The industrial process can be coal gasification, biomass gasification, or liquid fuel production by biomass fermentation, suitably ethanol production from a biomass such as corn.

Any suitable methanogenic archaea can be used, and a suitable temperature and pressure for the bioreactor condition can be selected depending at least in part on the methanogenic archaea selected. In some embodiments, suitably pressures within the bioreactor range from about 0.5 atmospheres to about 500 atmospheres. The bioreactor can also contain a source of intermittent agitation of the culture.

The culture conditions should suitably maintaining a redox potential of about −100 mV or less. In one embodiment, this redox potential is maintained by supplying a suitable amount of hydrogen gas.

Also in one embodiment, the methane gas removed from the bioreactor suitably comprises less than about 450 ppm hydrogen sulfide, or alternatively less than about 400 ppm, 300 ppm, 200 ppm, 150 ppm, 100 ppm, 50 ppm or 20 ppm of hydrogen sulfide.

Further, in certain embodiments the industrial output gas at least intermittently further comprises air and/or carbon monoxide. Suitably the industrial output gas comprises about 32% or less air by volume, or between from about 0.1% to about 32% air by volume, or less than about 4% air by volume, or at least about 4%, 8% or 16% air by volume. Suitably the industrial output gas can also comprise less than about 40% carbon monoxide by volume, or less than about 8% carbon monoxide by volume, or at least about 8% or 16% carbon monoxide by volume.

An another embodiment, the bioreactor comprises a culture of methanogenic archaea, a source of an output gas from an industrial process comprising CO$_2$ that feeds into the bioreactor, a source of hydrogen gas that feeds into the bioreactor, a gas feed from the bioreactor for removing gas from the bioreactor, a feed for providing fresh medium, and a feed for removing the culture.

DRAWINGS

Figure 15:
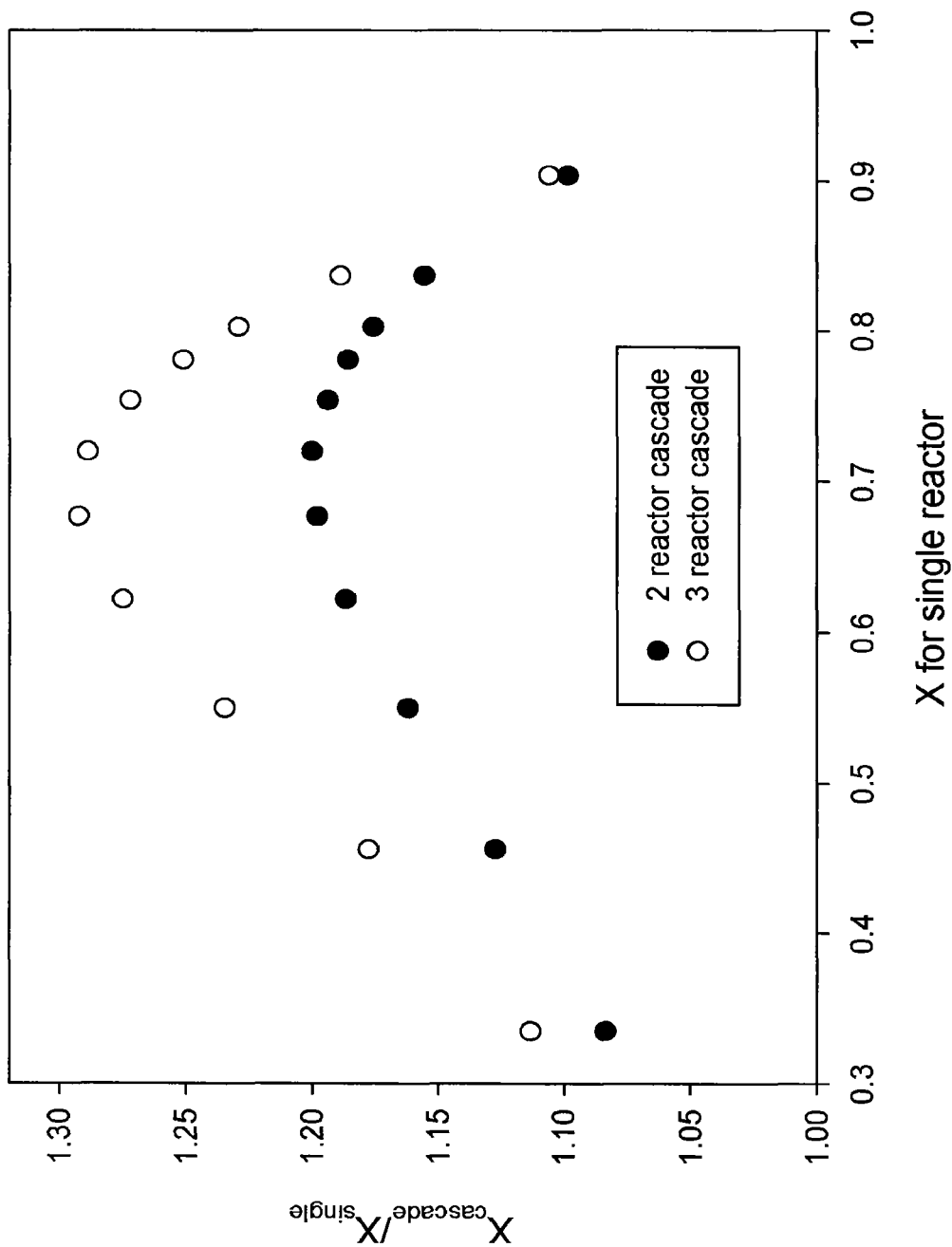

FIG. 15 is a chart showing a projected model of the extent of the conversion of hydrogen to methane in a two and three reactor cascade (Xcascade) divided by the extent of the conversion of hydrogen to methane in an equivalent total volume single reactor (Xsingle), the ratio plotted against Xsingle. Each of the single reactor cascade, 2 reactor cascade and 3 reactor cascade have the same total volume and same hydrogen input rate.

Figure 16:
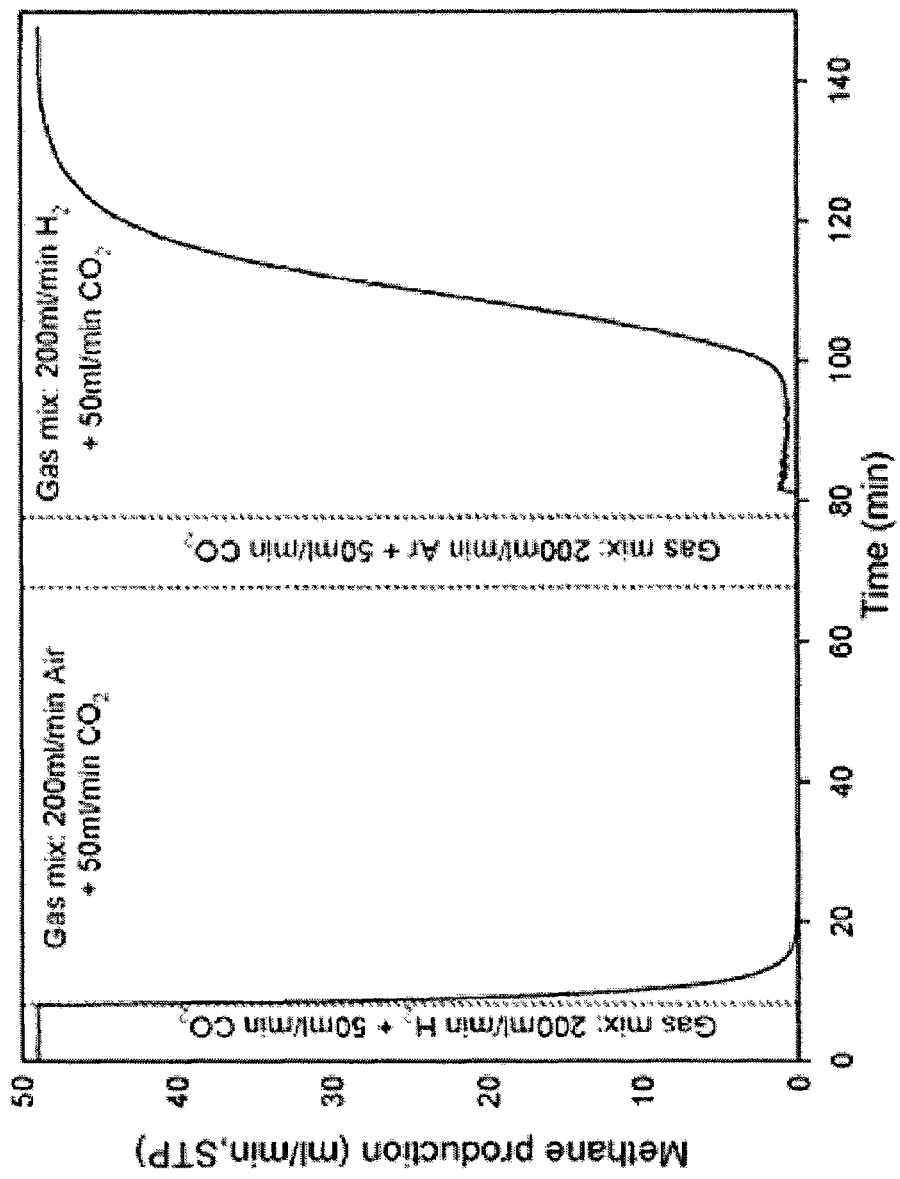

FIG. 16 is a chart showing the recovery of *Methanothermobacter thermoautotrophicus* after exposure to air.

DETAILED DESCRIPTION OF THE INVENTION

The present invention comprises a bioreactor system that can be integrated with industrial processes that produce $CO_2$ gas as a byproduct. In one embodiment such a process is the production of ethanol from biomass. The invention comprises a bioreactor containing a microbial culture capable of hydrogenotrophic methanogenesis (i.e. the conversion of $CO_2$ gas plus hydrogen gas to methane gas). The bioreactor is coupled to a hydrogen source and a $CO_2$ gas source. Suitably the $CO_2$ gas source is the $CO_2$ gas stream that is emitted by the production of ethanol. The hydrogen source is suitably hydrogen produced by the electrolysis of water. Suitably this hydrolysis is powered by electricity used in off peak times. The methane produced by the system can be fed back into the ethanol production facility to power various processes, and/or can be stored and sold as fuel.

Microbial cultures suitable for practice of the invention are readily obtainable from public collections of organisms or can be isolated from a variety of environmental sources. Such environmental sources include anaerobic soils and sands, bogs, swamps, marshes, estuaries, dense algal mats, both terrestrial and marine mud and sediments, deep ocean and deep well sites, sewage and organic waste sites and treatment facilities, and animal intestinal tracts and feces. Many pure cultures of single species are suitable. Classified pure cultures are all members of the Archaeal domain [Woese et al. Proc Natl Acad Sci USA 87:4576-4579 (1990) "Towards a natural system of organisms: Proposal for the domains Archaea, Bacteria, and Eucharya.", incorporated herein by reference] and fall within 4 different classes of the Euryarchaea kingdom. Examples of suitable organisms have been classified into 4 different genera within the Methanobacteria class (e.g. *Methanobacterium alcaliphilum, Methanobacterium bryantii, Methanobacterium congolense, Methanobacterium defluvii, Methanobacterium espanolae, Methanobacterium formicicum, Methanobacterium ivanovii, Methanobacterium palustre, Methanobacterium thermaggregans, Methanobacterium uliginosum, Methanobrevibacter acididurans, Methanobrevibacter arboriphilicus, Methanobrevibacter gottschalkii, Methanobrevibacter olleyae, Methanobrevibacter ruminantium, Methanobrevibacter smithii, Methanobrevibacter woesei, Methanobrevibacter wolinii, Methanothermobacter marburgensis, Methanothermobacter thermautotrophicum* (also known as *Methanothermobacter thermoautotroiphicus*), *Methanothermobacter thermoflexus, Methanothermobacter thermophilus, Methanothermobacter wolfeii, Methanothermus sociabilis*), 5 different genera within the Methanomicrobia class (e.g. *Methanocorpusculum bavaricum, Methanocorpusculum parvum, Methanoculleus chikuoensis, Methanoculleus submarinus, Methanogenium frigidum, Methanogenium liminatans, Methanogenium marinum, Methanosarcina acetivorans, Methanosarcina barkeri, Methanosarcina mazei, Methanosarcina thermophila, Methanomicrobium mobile*), 7 different genera within the Methanococci class (e.g. *Methanocaldococcus jannaschii, Methanococcus aeolicus, Methanococcus maripaludis, Methanococcus vannielii, Methanococcus voltaei, Methanothermococcus thermolithotrophicus, Methanocaldococcus fervens, Methanocaldococcus indicus, Methanocaldococcus infernus, Methanocaldococcus vulcanius*), and one genus within the Methanopyri class (e.g. *Methanopyrus kandleri*). Suitable cultures are available from public culture collections (e.g. the American Type Culture Collection, the Deutsche Sammlung von Mikroorganismen and Zellkulturen GmbH, and the Oregon Collection of Methanogens). Many suitable hydrogenotrophic methanogens, isolated in pure culture and available in public culture collections, have not yet been fully classified. Preferred pure culture organisms include *Methanosarcinia barkeri, Methanococcus maripaludis*, and *Methanothermobacter thermoautotrophicus*.

Suitable cultures of mixtures of two or more microbes are also readily isolated from the specified environmental sources [Bryant et al. Archiv Microbiol 59:20-31 (1967) "*Methanobacillus omelianskii*, a symbiotic association of two species of bacteria.", incorporated herein by reference]. Suitable mixtures may be consortia in which cells of two or more species are physically associated or they may be syntrophic mixtures in which two or more species cooperate metabolically without physical association. Mixed cultures may have useful properties beyond those available from pure cultures of known hydrogenotrophic methanogens. These properties may include, for instance, resistance to contaminants in the gas feed stream, such as oxygen, ethanol or other trace components, or aggregated growth, which may increase the culture density and volumetric gas processing capacity of the culture.

Suitable cultures of mixed organisms may also be obtained by combining cultures isolated from two or more sources. One or more of the species in a suitable mixed culture should be an Archaeal methanogen. Any non-Archael species may be bacterial or eukaryotic.

Suitable cultures may also be obtained by genetic modification of non-methanogenic organisms in which genes essential for supporting hydrogenotrophic methanogenesis are transferred from a methanogenic microbe or from a combination of microbes that may or may not be methanogenic on their own. Suitable genetic modification may also be obtained by enzymatic or chemical synthesis of the necessary genes.

The bioreactor system may provide continuous or discontinuous methane production using a continuous hydrogenotrophic methanogenic culture operating under stable conditions. An example of such suitable conditions is set forth below in the examples and is also provided in Schill, N., van Gulik, M., Voisard, D., & von Stockar, U. (1996) Biotechnol & Bioeng 51:645-658. "Continuous cultures limited by a gaseous substrate: development of a simple, unstructured mathematical model and experimental verification with *Methanobacterium thermoautotrophicum*", incorporated herein by reference. Culture media may be comprised of dilute mineral salts, and should be adapted to the particular culture in use.

The medium should be replenished at a rate suitable to maintain a useful concentration of essential minerals and to eliminate any metabolic products that may inhibit methanogenesis. Dilution rates below 0.1 culture volume per hour are suitable, since they yield high volumetric concentrations of active methane generation capacity. Surprisingly, dilution rates of less than 0.001 volumes was found to provide active methane generating capacity.

Total gas delivery rates ($CO_2$ plus $H_2$) in the range of 0.2 to 4 volume of gas (STP) per volume of culture per minute are suitable, since they both maintain and exploit high volumetric concentrations of active methane generation capacity.

In one embodiment, the redox potential is maintained below −100 mV or lower during methanogenesis. The method of the present invention encompasses conditions in which the redox potential is transiently increased to above −100 MV, as for example when air is added to the system.

In the examples below the temperature of the culture was maintained near the optimum for growth of the organism used in the culture (e.g. about 35° C. to about 37° C. for mesophilic organisms such as *Methanosarcinia barkeri* and *Methanococcus maripaludis* or about 60°-65° C. for thermophiles such as *Methanothermobacter thermoautotrophicus*, and about 85° C.-90° C. for organisms such as *Methanocaldococcus jannaschii, Methanocaldococcus fervens, Methanocaldococcus indicus, Methanocaldococcus infernus,* and *Methanocaldococcus vulcanius*). However, it is envisioned that temperatures above or below the temperatures for optimal growth may be used. In fact, higher conversion rates of methane may be obtained at temperatures above the optimal growth rate temperature.

In one embodiment of the invention, a reducing agent is introduced into the fermentation process along with $CO_2$ and hydrogen, this reducing agent can suitably be hydrogen sulfide or sodium sulfide. In one embodiment, a 4:1 mixture of $H_2$ and $CO_2$ gases can be provided at a total gassing rate (vvm) of from 0.1 L gas per L culture per minute [L/(L-min)] to >1.0 L/(L-min), with greater than 95% of the $CO_2$ converted to methane and the rest of the $CO_2$ in the input being converted to cellular biomass.

In another embodiment, hydrogen itself can be used as a reductant to maintain the redox potential of the culture in the range (<−100 mV) necessary for optimum performance of hydrogenotrophic methanogenesis. Generally, hydrogen gas is provided in the method in concentrations effective in allowing for at least a portion of the carbon dioxide in the bioreactor to be converted into methane.

In another embodiment, the redox potential of the culture can be maintained at <−100 mV via an electrochemical cell immersed in the medium.

In another embodiment, the system comprises various methods and/or features that reduce the presence of oxygen in the $CO_2$ stream that is fed into the bioreactor. When obligate anaerobic methanogenic microorganisms are used to catalyze methane formation, the presence of oxygen may be detrimental to the performance of the process and contaminates the product gas. Therefore the reduction of the presence of oxygen in the $CO_2$ stream is helpful for improving the process. In one embodiment, the oxygen level is reduced prior to entry of the gas into the fermentation vessel by passing the mixed $H_2/CO_2$ stream over a palladium catalyst, which converts any trace oxygen to water. In this embodiment, $H_2$ is provided in an amount above the amount needed in the culture by a 2:1 ratio relative to the contaminating oxygen. In another embodiment, the oxygen is removed by pre-treatment of the gas stream in a bioreactor. In this embodiment, the reductant may be provided either by provision of a source of organic material (e.g. glucose, starch, cellulose, fermentation residue from an ethanol plant, whey residue, etc.) that can serve as substrate for an oxidative fermentation. The microbial biological catalyst is chosen to oxidatively ferment the chosen organic source, yielding $CO_2$ from the contaminant oxygen. In this embodiment, additional $H_2$ would be provided to enable conversion in the anaerobic fermentor of this additional $CO_2$ to methane. In another embodiment, oxygen removal is accomplished in the main fermentation vessel via a mixed culture of microbes that includes one capable of oxidative fermentation of an added organic source in addition to the hydrogenotrophic methanogen necessary for methane production. An example of a suitable mixed culture was originally isolated as "*Methanobacillus omelianskii*" and is readily obtained from environmental sources [Bryant et al. Archiv Microbiol 59:20-31 (1967) "*Methanobacillus* omelianskii, a symbiotic association of two species of bacteria.", incorporated herein by reference]. In another embodiment, an oxygen tolerant methanogen is used in the bioreactor to improve the stability of the methane formation process in the presence of contaminating oxygen. Both *Methanosarcinia barkeri* and *Methanococcus maripaludis* are sufficiently oxygen tolerant in the presence of contaminating oxygen.

Figure 1:
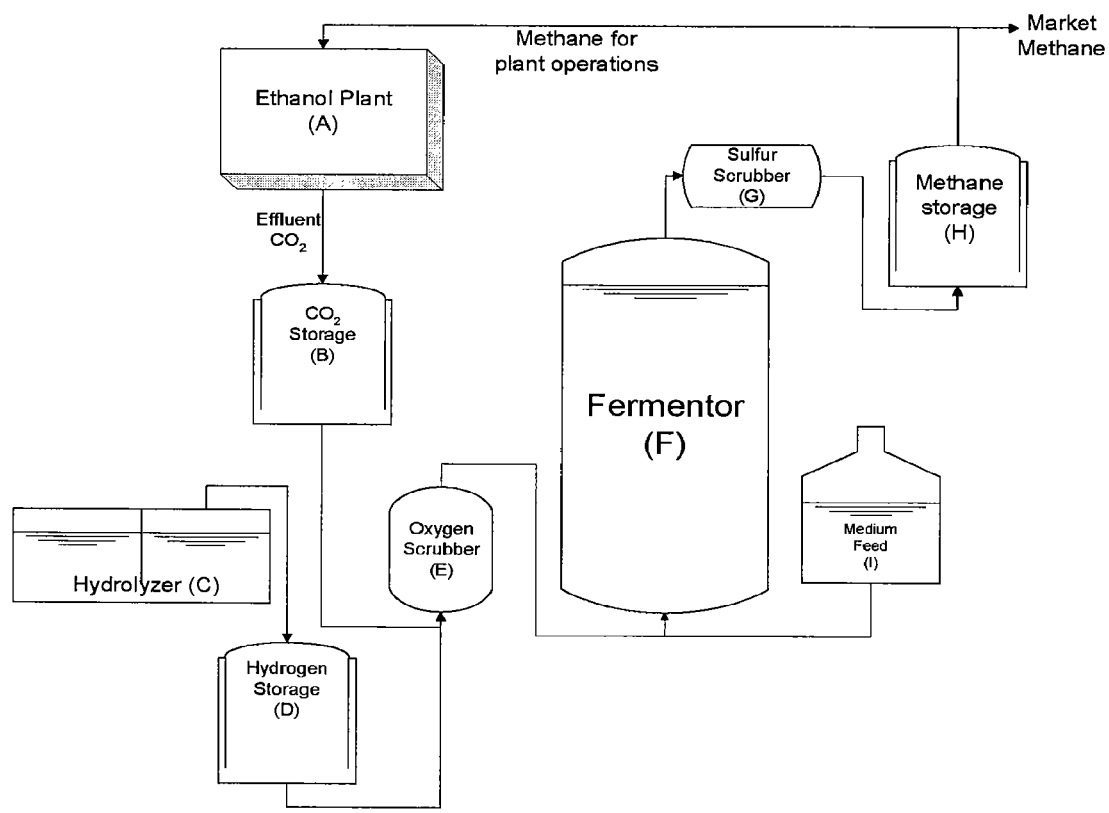
FIG. 1 shows a design schematic of one embodiment of a CO$_2$ recapture and methane production plant.

FIG. 1 depicts one embodiment of a $CO_2$ recapture and methane production plant using the methods set forth above. An industrial $CO_2$ source (A)—e.g. fuel ethanol plant—with $CO_2$ effluent and natural gas demand, vents $CO_2$ to a $CO_2$ collection and storage tank (B). A hydrolyzer (C) produces hydrogen, suitably from electrolysis. Hydrogen produce by the hydrolyzer (C) is collected in a hydrogen storage tank (D). The hydrogen and $CO_2$ from their respective storage tanks are fed through an oxygen scrubber (E) for removal of oxygen from the $CO_2$ effluent stream. After passing through the oxygen scrubber (E), the hydrogen and $CO_2$ are feed into a fermentor/bioreactor system (F) for conversion of $CO_2+H_2$ to methane. A storage tank providing medium (I) is also connected to the fermentor/bioreactor system (F) to provide for replenishment of nutrients in the fermentor. The methane gas vented from the fermentor/bioreactor (F) passes through a sulfur scrubber (G) for recovering sulfur from the product methane stream. The methane gas can then be stored in a methane storage tank (H).

A bioreactor, also known as a fermentor vessel, as set forth in the invention is any suitable vessel in which methanogenesis can take place. Suitable bioreactors to be used in the present invention should be sized relative to the volume of the $CO_2$ source. Typical streams of 2,200,000 lb $CO_2$/day from a 100,000,000 gal/yr ethanol plant would require a $CO_2$ recovery/methane production fermentor of about 750,000 gal total capacity. Fermentor vessels similar to the 750,000 gal individual fermentor units installed in such an ethanol plant would be suitable.

Figure 2:
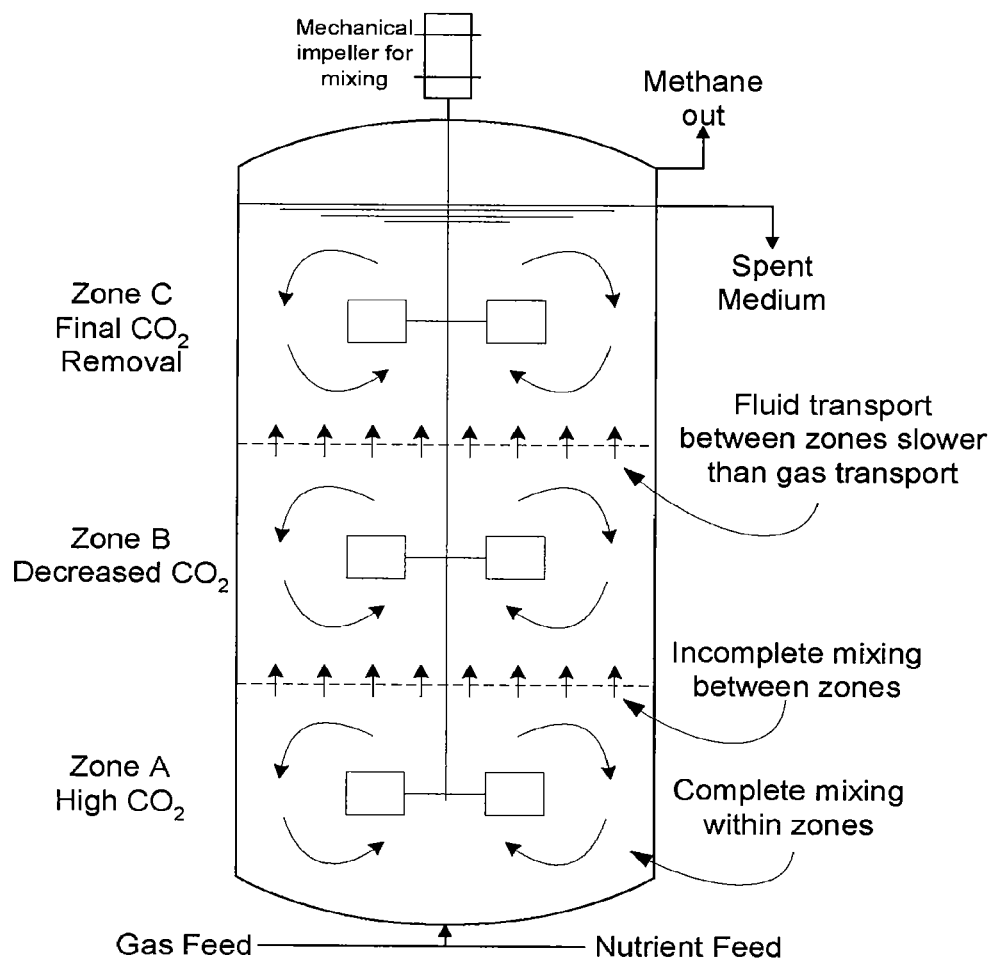
FIG. 2 shows a design schematic of one embodiment of a stratified bioreactor.

FIG. 2 depicts one embodiment of a stratified bioreactor that can be used in the present invention. In this embodiment, the bioreactor has the $CO_2$ and hydrogen entering into the bottom of the bioreactor along with the nutrients for the bioreactor. A mechanical impeller is positioned on the top of the bioreactor and is used to move a mixing apparatus within the bioreactor. The bioreactor has three zones, A, B and C. Zone A at the bottom of the reactor is a high $CO_2$ zone. Zone B, in the middle of the bioreactor has a decreased $CO_2$ presence, and Zone C at the top end of the reactor has little if any $CO_2$. The methane produced, and the spent medium is removed from the top of the bioreactor.

Figure 3:
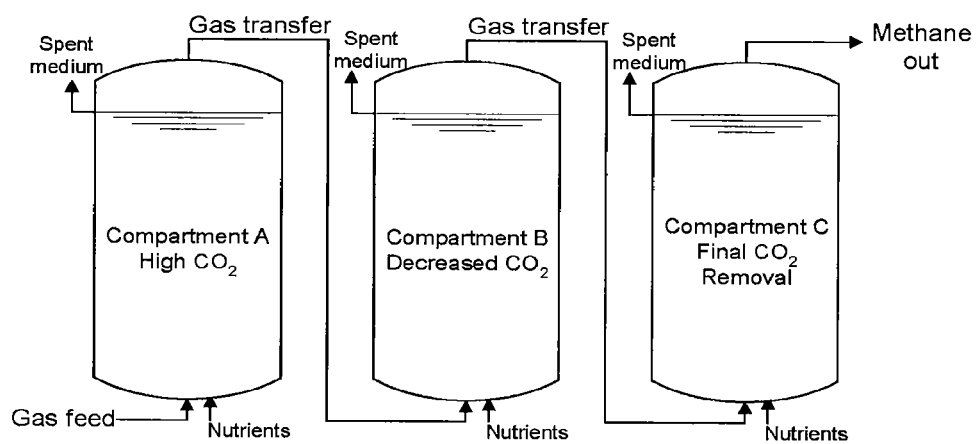
FIG. 3 shows a design schematic of a system of bioreactors set up in cascaded serial arrangement.

FIG. 3 depicts one embodiment of a cascaded bioreactor that can be used in the present invention. In this embodiment, the hydrogen, $CO_2$ and cell nutrients are fed into the bottom of a first compartment (A). In this compartment (A), even after fermentation, there is still a high level of $CO_2$. The gas produced by the fermentation reaction in the first compartment (A) is then transferred from the top of the first compartment to the bottom of a second compartment (B) along with cell nutrients. In this second compartment (B) the $CO_2$ level is decreased from the levels found in the first compartment (A). The gas produced by the fermentation reaction in the second compartment (B) is transferred from the top of the second compartment (B) to the bottom of a third compartment (C) along with cell nutrients. In this third compartment (C) most if not all of the $CO_2$ has been removed and only the methane gas is left to be removed from the top of the compartment. In each of the compartments, spent medium can be removed from the compartments.

Example 1—General Setup for Bench Scale Bioreactor

A bench-scale bioreactor was used to test a series of variables important in the design and operation of an industrial scale bioreactor. A 1.3 L fermenter vessel (bioreactor) (BioFlo 110, New Brunswick), fitted with an Ingold autoclavable pH electrode for measuring pH in the medium and a Lazar Labs double junction platinum band autoclavable ORP electrode for measuring the oxidation-reduction potential (ORP) of the medium was used in the following experiments. The bioreactor contained 1 L culture medium and was stirred at 400 rpm with a Rushton impeller. With 1 L of medium, the bioreactor has a headspace of 300 cc of gas. The chamber was also fitted with a peristaltic pump that could control the addition of a chemical reductant, such as $Na_2S$. A second peristaltic pump controlled the constant addition of fresh culture medium to the vessel to enable continuous culture operation. A third peristaltic pump was used to remove excess liquid from the culture vessel, maintaining a constant volume of 1 L. The excess liquid included the metabolic water generated during methanogenesis as well as increased medium volume from continuous culture operation. The temperature of the culture was controlled by a heating blanket. Gas mixtures were introduced via a sparger at the bottom of the vessel. The composition of the gas mixture was controlled by three mass flow controllers, one for $H_2$, one for $CO_2$, and a third that could be used for controlling addition of air, CO, or $N_2$. Generally, a gas composition of 1 volume $CO_2$ to 4 volumes of $H_2$ was used and was passed over a palladium catalyst (Alfa AESAR) prior to introduction to the culture. The culture in the bioreactor was maintained at about 1 atmosphere of pressure. The gas exiting the culture vessel at ambient atmospheric pressure was passed through a condenser at 4° C. to reduce water vapor content. The composition of the effluent gas stream was analyzed by a Cirrus quadrupole mass spectrometer continually scanning the mass range of 1 to 50 atomic mass units. To correct for variations in ambient pressure over time, each scan was normalized to the sum of detected masses. Composition of individual gasses was determined by comparison with mixtures of various composition generated with the mass flow control system. Measurements were made of the amount of methane produced by a given volume of culture per unit time, as well as the efficiency of conversion of input $CO_2$ and $H_2$ to methane.

Example 2—Bench Scale Bioreactor Using *Methanococcus maripaludis*

The general setup of Example 1 was used with the organism *Methanococcus maripaludis*. *Methanococcus maripaludis* is grown at 37° C. in modified McCas medium containing the following components per L of medium: KCl 0.335 g, $MgCl_2·6H_2O$ 2.75 g, $MgSO_4·7H2O$ 3.45 g, $CaCl_2·2H_2O$ 0.14 g, $NH_4Cl$ 0.5 g, $NaHCO_3$ 8.4 g, NaCl 22 g, $K_2HPO_4$ 0.14 g, $FeSO_4·7H_2O$ 9.5 mg, Resazurin 1 mg, Casamino acids 2 g, cysteine·$H_2O$·HCl 0.5 g, $Na_3$Citrate·$2H_2O$ 21 mg, $MnSO_4·2H_2O$ 5 mg, $CoCl_2(·6H_2O)$ 1 mg, $ZnSO_4(·7H2O)$ 1 mg, $CuSO_4·5H_2O$ 0.1 mg, AlK$(SO_4)_2$ 0.1 mg, $H_3BO_4$ 0.1 mg, $Na_2MoO_4·2H_2O$ 1 mg, $NiCl_2·6H_2O$ 0.25 mg, $Na_2SeO_3$ 2 mg, V(III)Cl 0.1 mg, $Na_2WO_4·2H_2O$ 1 mg, biotin 0.02 mg, folic acid 0.02 mg, pyridoxine HCl 0.10 mg, thiamine HCl 0.05 mg, riboflavin 0.05 mg, nicotinic acid 0.05 mg, DL-calcium pantothenate 0.05 mg, vitamin B12 0.001 mg, p-aminobenzoic acid 0.05 mg, lipoic acid 0.05 mg. After autoclaving and before inoculation, the medium was reduced by the addition of 0.5 g/L $Na_2S$ from a 50× anaerobic, sterile stock solution, yielding an ORP of the medium below −100 mV. The medium was equilibrated prior to inoculation with a gas phase containing 0.2 atmosphere partial pressure of $CO_2$ to yield a pH in the range of 7.2-7.3. The initial medium used to start the culture contained, in addition to the above components, 1.4 g/L NaAcetate·$3H_2O$, but the medium reservoir used in continuous culture conditions lacked the addition of acetate.

Figure 4:
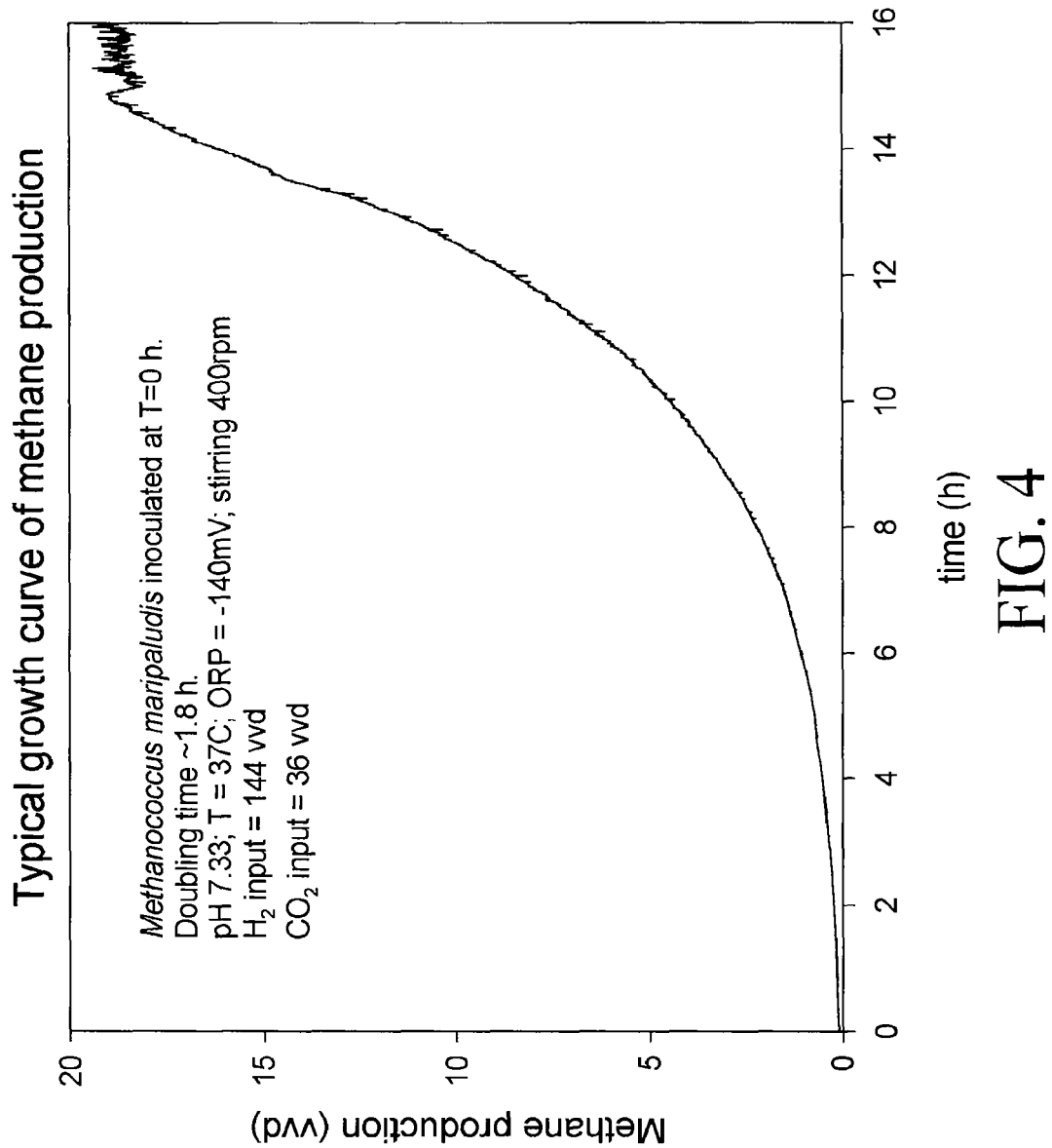
FIG. 4 is a chart showing the growth curve of methane production of *Methanococcus maripaludis*.

1 L of the fresh medium was initially inoculated with 5 mL of *Methanococcus maripaludis* in a stationary phase, and methane production was monitored over time. As shown in FIG. 4, a gas feed of 4:1 $H_2:CO_2$ (125 cc/min or 180 volumes of gas (STP) per volume of culture per day (VVD), 144 vvd $H_2$ and 36 vvd $CO_2$) was provided at a culture of pH 7.33 and an ORP of −140 mV. During the growth phase, the rate of methane production is limited by the available biological catalysts for the reaction. The methane production rate stabilized once the dissolved hydrogen in the medium was depleted. The stabilized rate is limited by the physical process of gas-to-liquid mass transfer of hydrogen, rather than by biological factors. Once this transition to stable methane production was observed, the culture was switched to continuous culture conditions in which fresh medium was added at a constant rate of 0.94 ml/h, or 22.5 ml/day. It was found that a slower input of fresh culture medium led to a denser culture and hence better volumetric performance. At the limit of no fresh medium, however, it was found that the culture ultimately dies.

Example 3: Effect of Agitation on Methane Production of *Methanococcus maripaludis*

Figure 5:
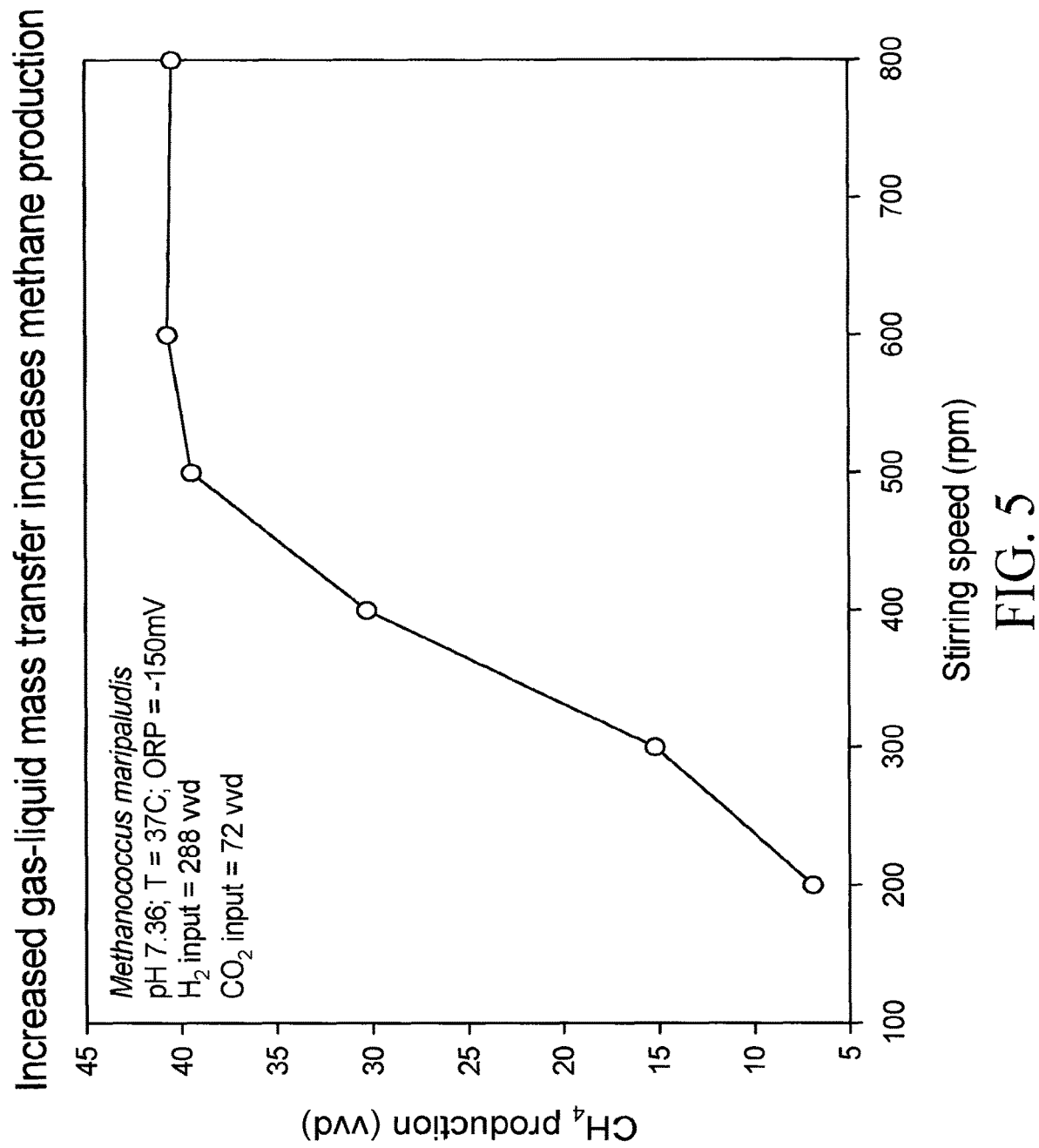
FIG. 5 is a chart demonstrating the effects of agitation of a culture of *Methanococcus maripaludis* with respect to methane production.

The turbidity of the culture obtained in Example 2 continued to increase after the gas-to-liquid mass transfer-limited rate of methane production was reached, providing an excess of biological catalytic capacity. This additional catalytic capacity can be accessed by changing physical parameters that increase the gas-to-liquid mass transfer rate. As shown in FIG. 5, the mixing rate in the culture was varied from the standard 400 rpm. A total feed rate of a 4:1 $H_2$:$CO_2$ gas mixture (250 cc/min (288 vvd $H_2$; 72 vvd $CO_2$)) was used. At this gas feed rate, the conversion efficiency of both $CO_2$ and hydrogen reaches 55-56% at higher mixing speeds demonstrating that higher stirring rates increases the gas-to-liquid mass transfer and therefore higher methane production. Other abiotic methods that may be used to increase the gas-to-liquid mass transfer and hence the methane production rate include 1) increased gas pressure and 2) increased temperature. Some methanogenic archaea can thrive at pressures over 500 atmospheres. With respect to different temperature conditions, thermophilic methanogens, such as *Methanothermobacter thermoautotrophicus* (at about 60° C.-65° C.) or *Methanocaldococcus jannaschii* (at about 85°-90° C.), can be used as the biological catalyst.

Example 4—Conversion Efficiency of $H_2$ by *Methanococcus maripaludis*

Figure 6:
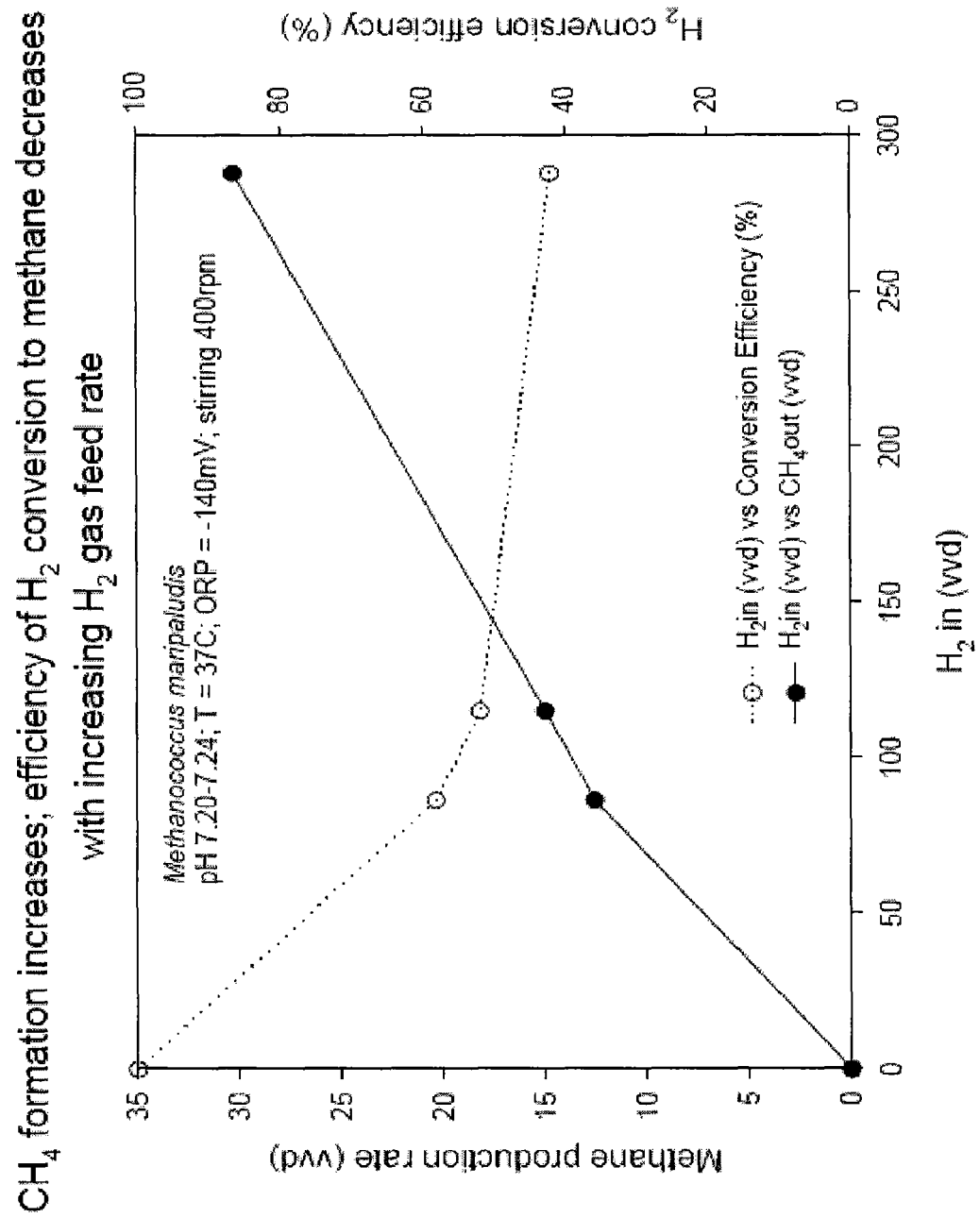
FIG. 6 is a chart showing the changes in hydrogen conversion to methane catalyzed by *Methanococcus maripaludis* with respect to changes in the feed rate hydrogen gas into the bioreactor.

A culture of *Methanococcus maripaludis* was setup in a bioreactor as set forth in Example 2. As shown in FIG. 6, gas was fed to a mature culture at varying rates, maintaining a 4:1 hydrogen to carbon dioxide ratio. Once the culture was above the gas-liquid mass transfer-limited cell density, it was found that methane production could be increased by increasing the $H_2$ gas feed rate. However, at higher $H_2$ gas feed rates, it was found that a decreasing proportion of the $H_2$ gas was converted to methane. The converse was also found to be true, that at lower gas feed rates, hydrogen was converted more efficiently to methane. Because the volume of feed gas (4 volumes of hydrogen plus 1 volume of $CO_2$) decreases as it is converted to methane (1 volume of methane product), a cascade or stratified bioreactor system as shown in FIG. 2 and FIG. 3 is advantageous. In a serial bioreactor system as shown in FIG. 3, the residual hydrogen in the effluent gas from a first fermenter would provide a lower feed rate to a second fermenter and would therefore be converted at higher efficiency in the second fermenter. This phenomenon can be used to obtain a highly efficient conversion in a cascaded fermenter design Example 5: Bench Scale Bioreactor Using *Methanosarcina barkeri*

The general setup of Example 1 was used with the organism *Methanosarcina barkeri*. *Methanosarcina barkeri* (strain DSM 804 obtained from the Deutsche Sammlung von Mikroorganismen and Zellkulturen GmbH) was grown at 35° C. in MS enriched medium containing the following components per L of medium: $NaHCO_3$ 8.4 g, yeast extract 2.0 g, trypticase peptones 2.0 g, mercaptoethanesulfonic acid 0.5 g, $NH_4Cl$ 1.0 g, $K_2HPO_4 \cdot 7H_2O$ 0.4 g, $MgCl_2 \cdot 7H_2O$ 1.0 g, $CaCl_2 \cdot 2H_2O$ 0.4 g, Resazurin 1 mg, cysteine·$H_2O$·HCl 0.25 g, $Na_2EDTA \cdot 2H_2O$ 5 mg, $MnCl_2 \cdot 4H_2O$ 1 mg, $CoCl_2$ (·$6H_2O$) 1.5 mg, $FeSO_4 \cdot 7H_2O$ 1 mg, $ZnCl_2$ 1 mg, $AlCl_3 \cdot 6H_2O$ 0.4 mg, $Na_2WO_4 \cdot 2H_2O$ 0.3 mg, CuCl 0.2 mg, $NiSO_4 \cdot 6H_2O$ 0.2 mg, $H_2SeO_3$ 0.1 mg, $H_3BO_4$ 0.1 mg, $Na_2MoO_4 \cdot 2H_2O$ 0.1 mg, biotin 0.02 mg, folic acid 0.02 mg, pyridoxine HCl 0.10 mg, thiamine HCl 0.05 mg, riboflavin 0.05 mg, nicotinic acid 0.05 mg, DL-calcium pantothenate 0.05 mg, vitamin B12 0.001 mg, p-aminobenzoic acid 0.05 mg, lipoic acid 0.05 mg. After autoclaving and before inoculation, the medium was reduced by the addition of 0.5 g/L $Na_2S$ from a 50× anaerobic, sterile stock solution, yielding an ORP of the medium below −100 mV. The medium was equilibrated prior to inoculation with a gas phase containing 0.2 atmosphere partial pressure of $CO_2$ to yield a pH in the range of 6.8-7.0.

1 L of the fresh medium was initially inoculated with 20 mL *Methanosarcina barkeri* in a stationary phase, and methane production was monitored over time. Once the transition to stable methane production was observed, the culture was switched to continuous culture conditions in which fresh medium was added at a constant rate of 0.94 ml/h, or 22.5 ml/day. It was found that a slower input of fresh culture medium led to a denser culture and hence better volumetric performance. At the limit of no fresh medium, however, it was found that the culture ultimately dies.

Example 6—Recovery from Oxygen Exposure—Recovery of *Methanosarcina barkeri* with Exposure of 10 Minutes of Air Methanogenic organisms are regarded as extremely strict anaerobes. Oxygen is known as an inhibitor of the enzyme catalysts of both hydrogen uptake and methanogenesis. A low oxidation-reduction potential (ORP) in the growth medium is regarded as important to methanogenesis. Air is a possible contaminant of carbon dioxide streams that could be used to support energy storage in the form of methane and so the effects of air on the capacity of the cultures to produce methane was examined.

Figure 7:
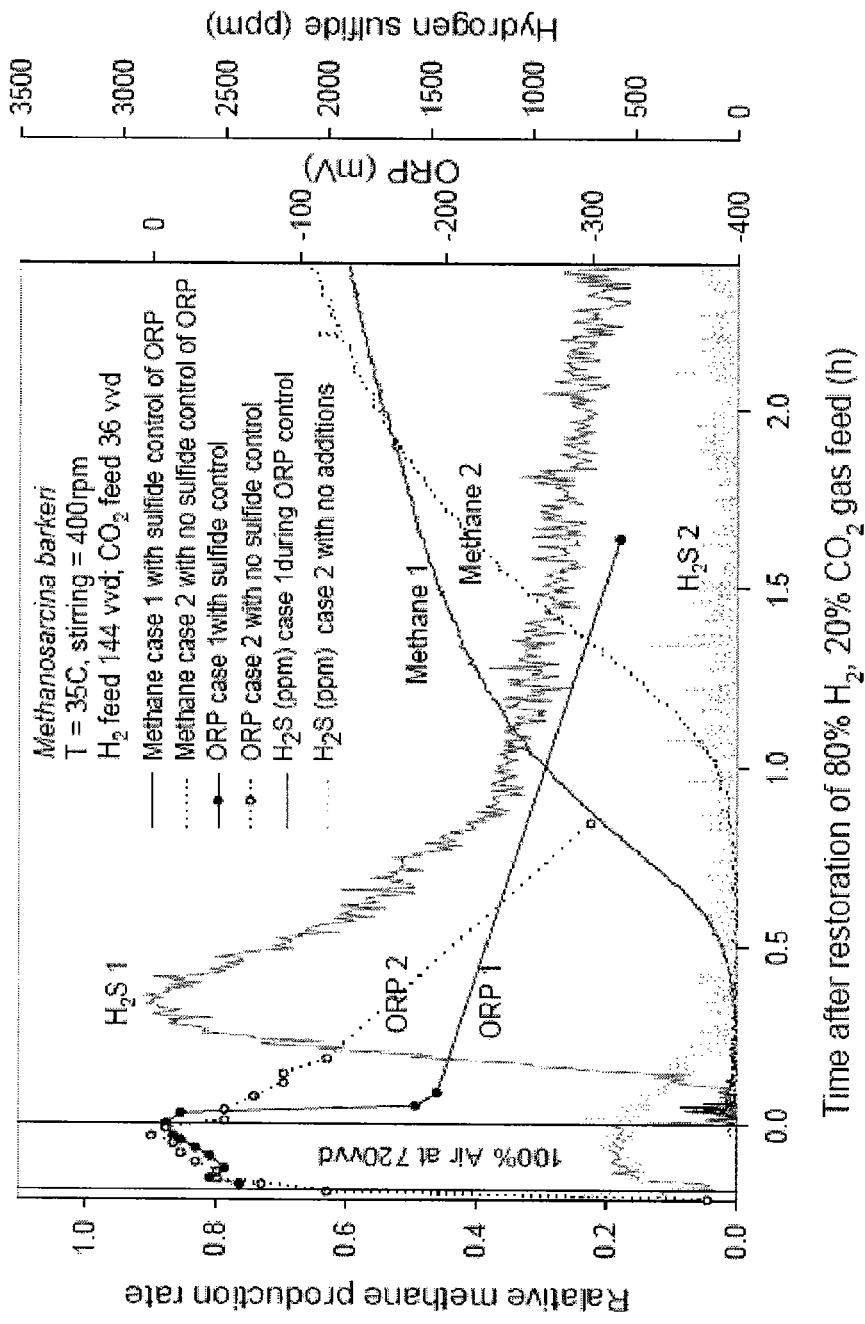
FIG. 7 is a chart showing the recovery of methanogenesis in a culture *Methanosarcina barkeri* after exposure to 10 minutes of 100% air.

FIG. 7 shows the recovery of the methanogenic activity of *Methanosarcina barkeri* after exposure to air. A bench bioreactor containing *Methanosarcina barkeri* was prepared as set forth in Example 5. Two experiments were performed involving exposing the culture to 100% air for 10 minutes at a flow rate of 500 cc/min. Ambient air comprises approximately (by molar content/volume) 78% nitrogen, 21% oxygen, 1% argon, 0.04% carbon dioxide, trace amounts of other gases, and a variable amount (average around 1%) of water vapor. During exposure to 100% air, methanogenesis stopped and the ORP of the culture medium rose. The air used in the experiment also displaces $CO_2$ dissolved in the medium, causing the pH to rise (not shown in this figure). Following the 10 minute exposure to 100% air, gas flows of $H_2$ and $CO_2$ were restored (100 cc/min $H_2$, 25 cc/min $CO_2$).

In the first experiment, 1.5 ml of a 2.5% solution of sulfide ($Na_2S \cdot 7H_2O$) was added within 4 minutes of terminating air feed and restoring the $H_2/CO_2$ gas feed. Sulfide is widely used to control the ORP of the cultures, control that is regarded as essential. In another experiment, no sulfide was added. The dotted curves show a case in which no sulfide was added and the solid line shows the recovery of the culture where sulfide was added. In both cases, methanogenesis recovers. The figure shows that addition of sulfide for ORP control in case 1 causes the emitted hydrogen sulfide to rise to 3000 ppm. In the case of ORP control with hydrogen (no sulfide addition), the hydrogen sulfide level is at or below the limit of detection of the mass spectrometer under these operating conditions (50-100 ppm). Methanogenesis begins to recover more quickly in the case of ORP control with sulfide, but the experiment shows that sulfide is not essential for recovery. The presence of the hydrogen in the gas phase is sufficient to reduce the ORP of the culture to enable methanogenesis, no additional control of the ORP of the culture is required. The lack of necessity of sulfide is of note in that methanogenic cultures are typically maintained at 10,000 ppm hydrogen sulfide in the gas phase. Such high levels of sulfide are not tolerated in certain industrial process, for instance, natural gas pipeline tariffs in the United States set maximum levels of hydrogen sulfide content of natural gas ranging from 4-16 ppm, depending upon the pipeline system.

Figure 8:
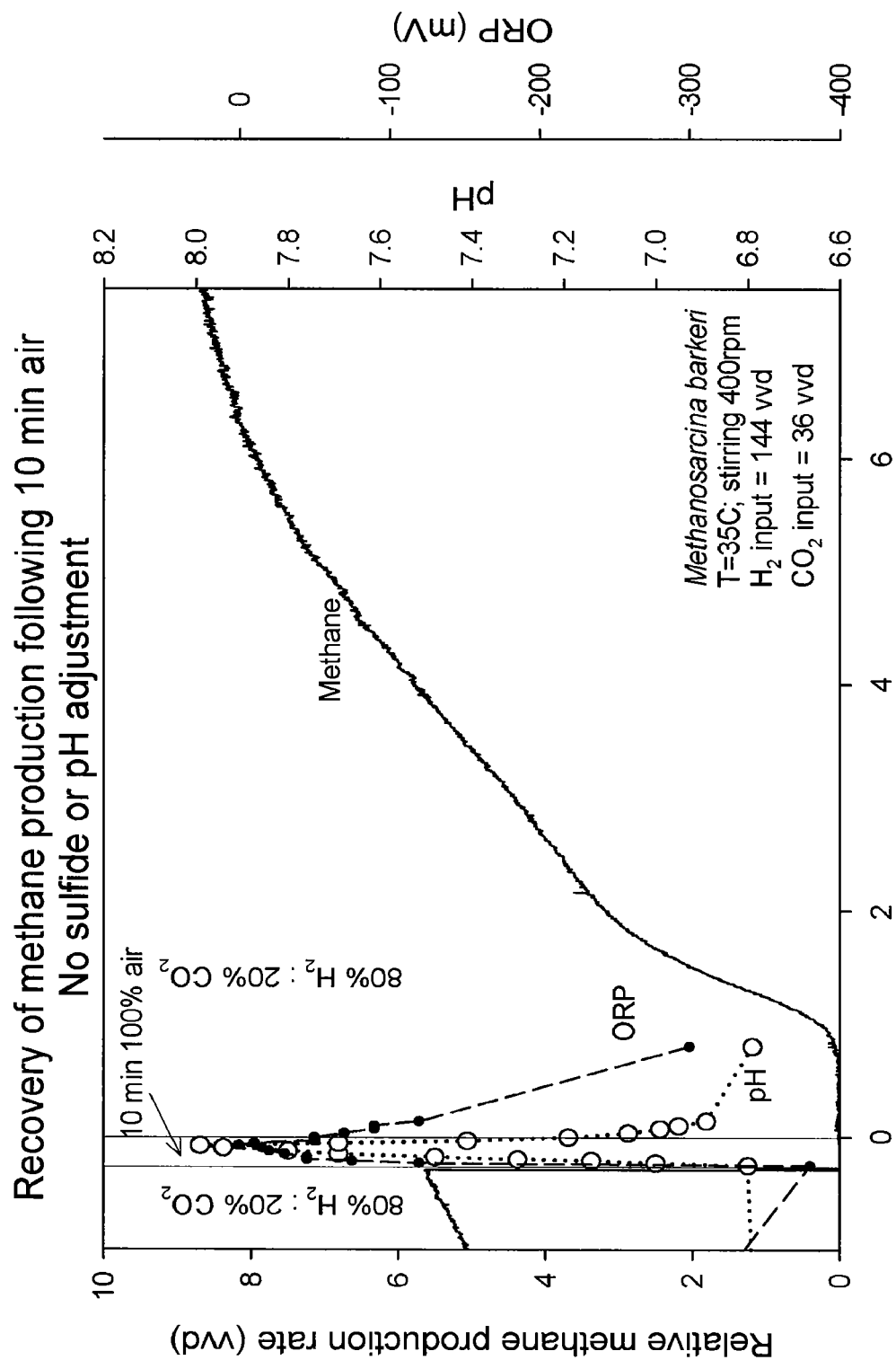
FIG. 8 is a chart showing the recovery of methanogenesis in a culture *Methanosarcina barkeri* after exposure to 10 minutes of 100% air.

FIG. 8 also shows the recovery of *Methanosarcina barkeri* after the air exposure above (absent the addition of sulfide) after 7 hours.

Figure 9:
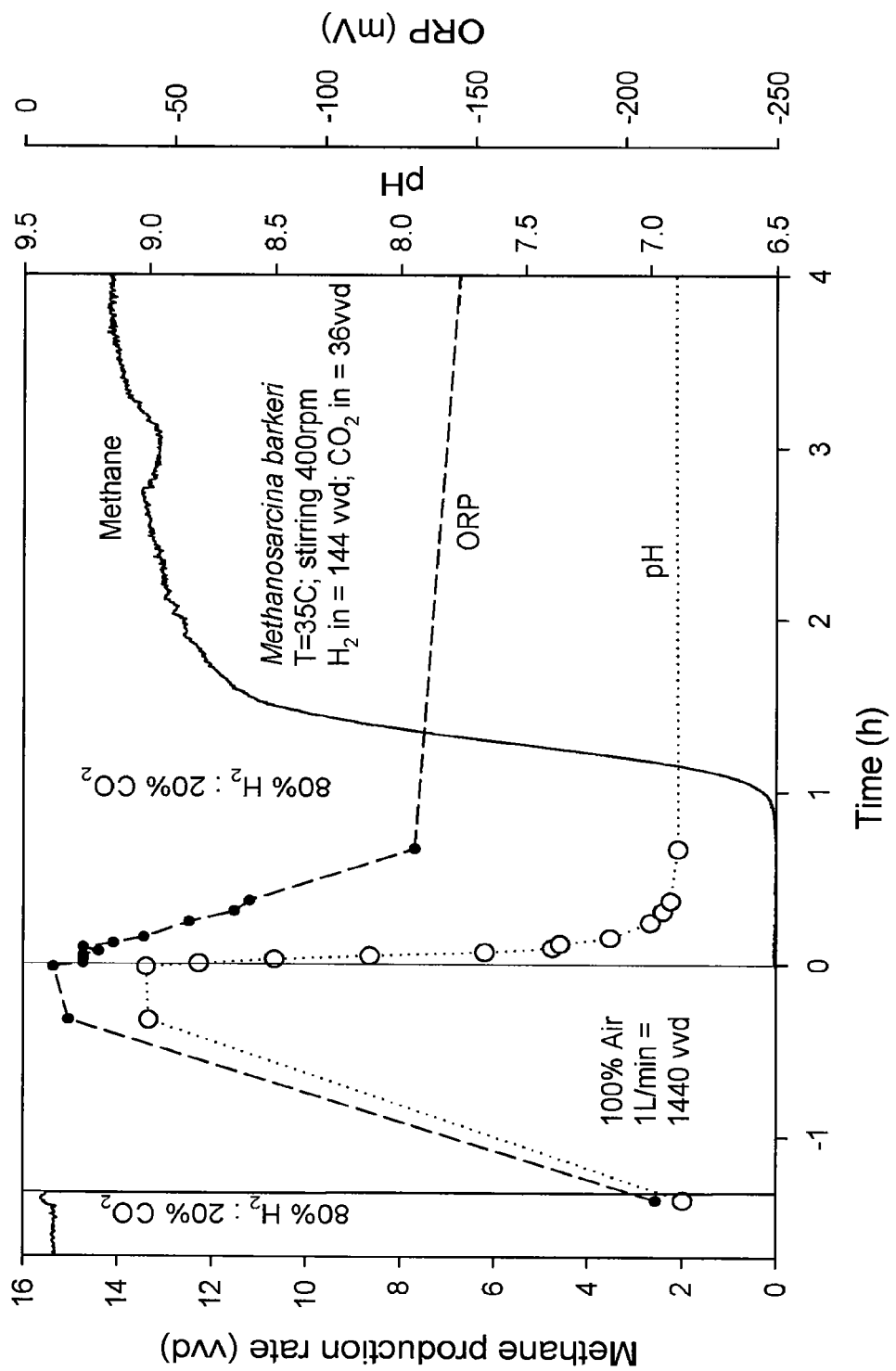
FIG. 9 is a chart showing the recovery of methanogenesis in a culture *Methanosarcina barkeri* after exposure to 90 minutes of 100% air.

Example 7—Recovery from Oxygen Exposure—Recovery of *Methanosarcina barkeri* with Exposure of 90 Minutes of Air FIG. 9 shows the recovery of *Methanosarcina barkeri* after 15 hours of exposure to air. A bench bioreactor containing *Methanosarcina barkeri* was prepared as set forth in Example 5. The culture was exposed to 100% air for 90 minutes introduced at 1 L/min (1440 vvd). During exposure to 100% air, methanogenesis stopped and the ORP of the culture medium rose. The air used in the experiment also displaced $CO_2$ dissolved in the medium, causing the pH to rise. Following the 90 minute exposure to 100% air, gas flows of $H_2$ and $CO_2$ were restored (100 cc/min $H_2$ (144 vvd) and 25 cc/min $CO_2$ (36 vvd). Restoration of hydrogen as a reductant was sufficient to reduce the ORP to levels that favor methanogenesis. Methane production began within 1 hr of restoring 4:1 $H_2$:$CO_2$ gas phase (100 cc/min $H_2$, 25 cc/min $CO_2$). Full recovery of methane production was achieved within 3-4 hrs.

Figure 10:
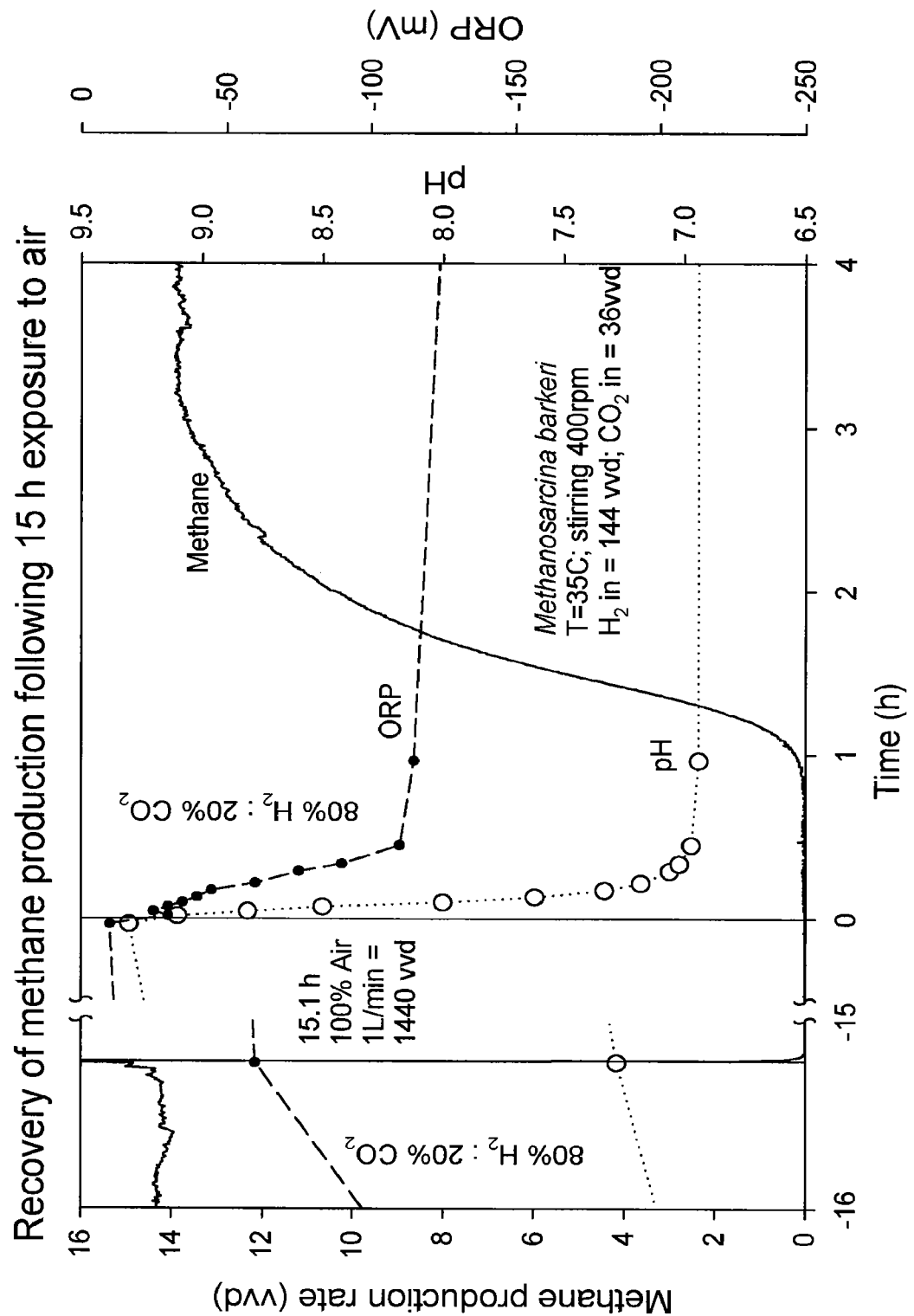
FIG. 10 is a chart showing the recovery of methanogenesis in a culture *Methanosarcina barkeri* after exposure to 15 hours of 100% air.

Example 8—Recovery from Oxygen Exposure—Recovery of *Methanosarcina barkeri* with Exposure of 15 Hours of Air FIG. 10 shows the recovery of *Methanosarcina barkeri* after 15 hours of exposure to air. A bench bioreactor containing *Methanosarcina barkeri* was prepared as set forth in Example 5. The culture was exposed to 100% air for 15.1 hours at a flow rate of 1 L/min. During exposure to 100% air, methanogenesis stopped and the ORP of the culture medium rose to about −10 mV. The air used in the experiment also displaced $CO_2$ dissolved in the medium, causing the pH to rise to 9.3. Following the 15.1 hour exposure to 100% air, gas flows of $H_2$ and $CO_2$ were restored (100 cc/min $H_2$, 25 cc/min $CO_2$). Restoration of hydrogen as a reductant was sufficient to reduce the ORP to levels that favor methanogenesis. Methane production began within 1.1 hr of restoring 4:1 $H_2$:$CO_2$ gas phase (100 cc/min $H_2$, 25 cc/min $CO_2$). Full recovery of methane production was achieved within 3 hrs.

Figure 11:
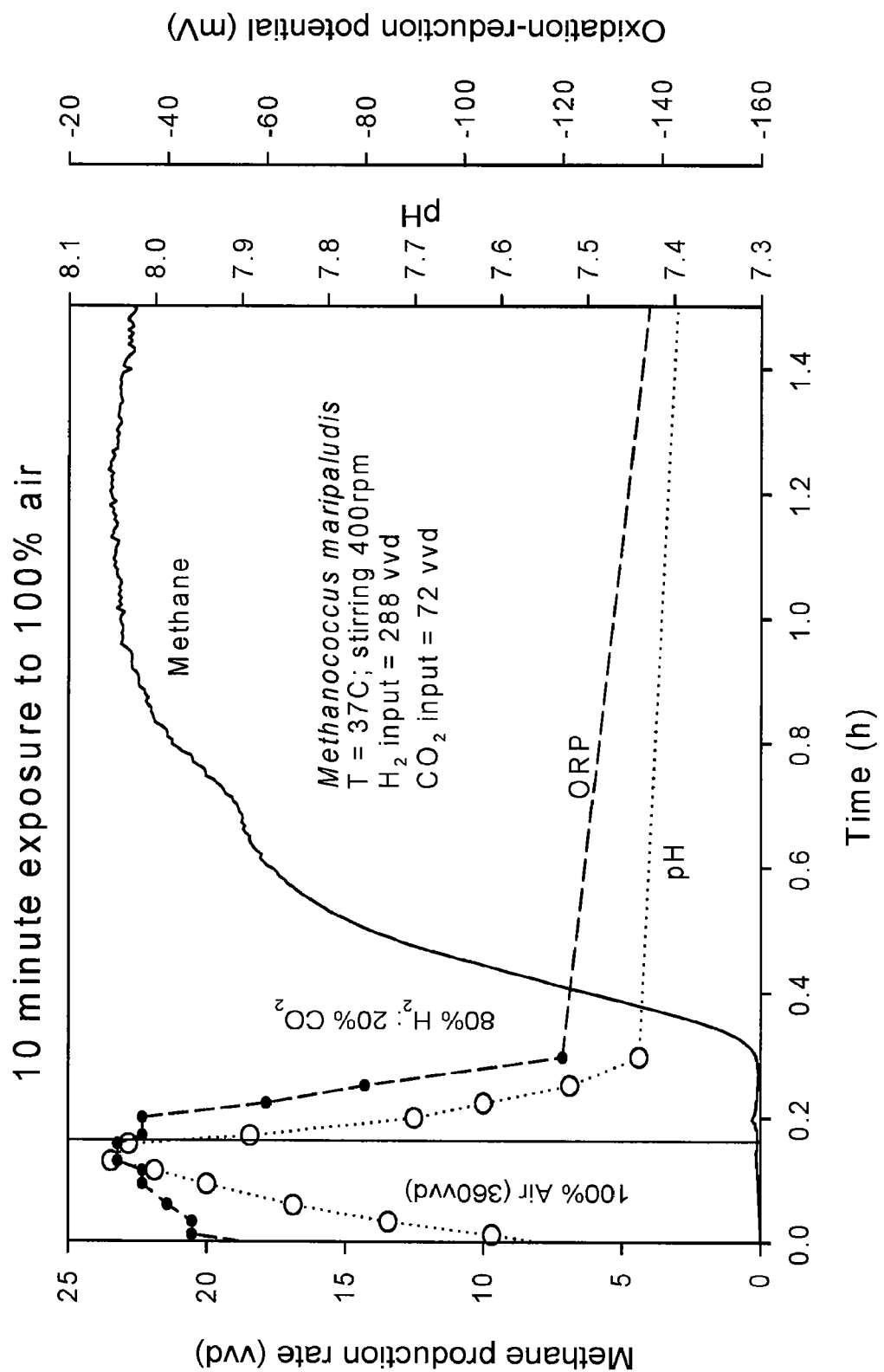
FIG. 11 is a chart showing the recovery of methanogenesis in a culture *Methanococcus maripaludis* after exposure to 10 minutes of 100% air.

Example 9—Recovery from Oxygen Exposure—Recovery of *Methanococcus maripaludis* with Exposure of 10 Minutes of Air FIG. 11 shows the recovery of the methanogenic activity of *Methanococcus maripaludis* after exposure to air. A bench bioreactor containing *Methanococcus maripaludis* was prepared as set forth in Example 2. The culture was exposed to 100% air for 10 minutes at 360 vvd. During exposure to 100% air, methanogenesis stopped and the ORP of the culture medium rose. The air used in the experiment also displaces $CO_2$ dissolved in the medium, causing the pH to rise. Following the 10 minute exposure to 100% air, gas flows of $H_2$ and $CO_2$ were restored (288 vvd $H_2$, 72 vvd $CO_2$). Methanogenesis in was shown to have recovered within 10 min, with full recovery of methane production rate occurring within 1.5 hours.

Figure 12:
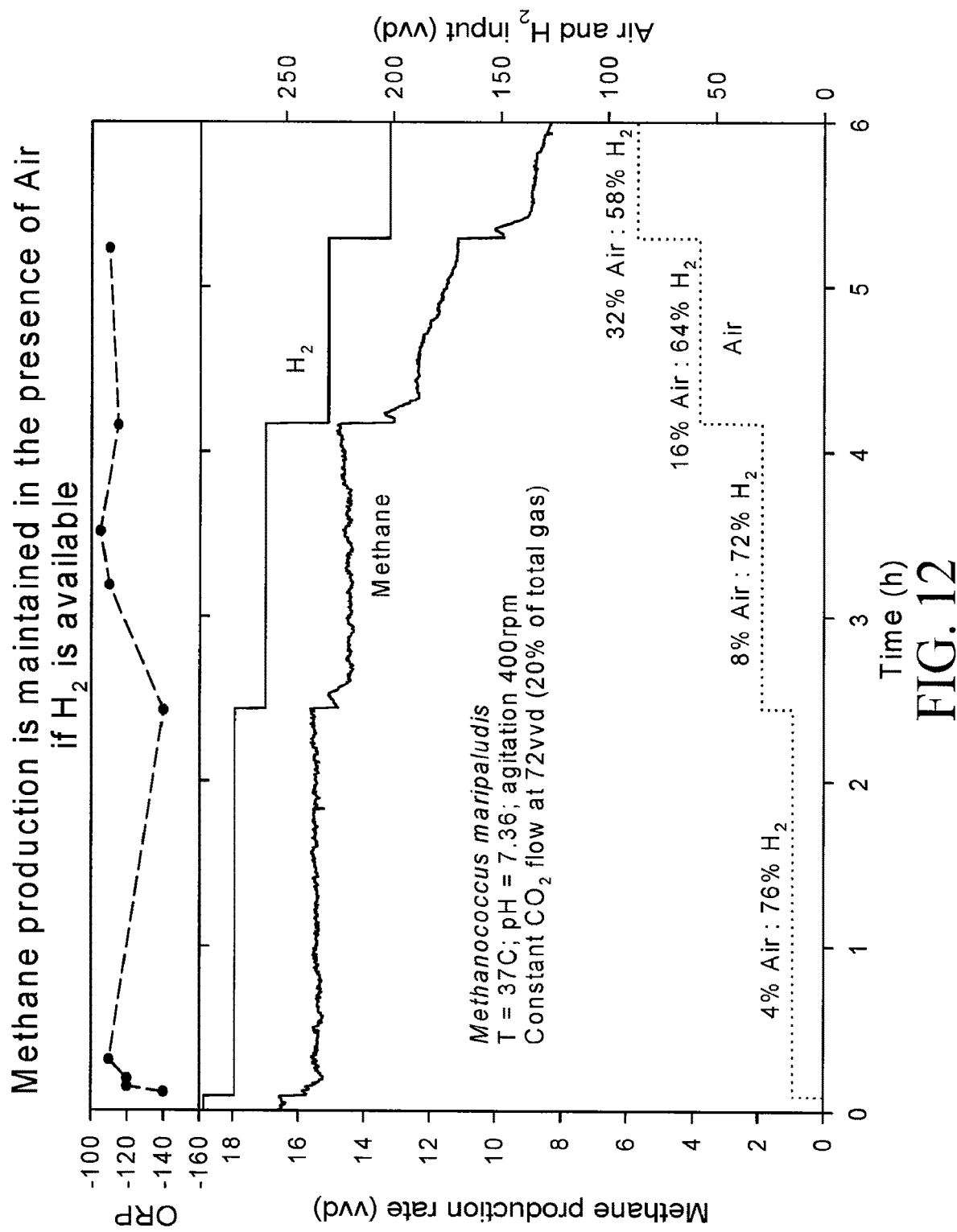
FIG. 12 is a chart showing the recovery of methanogenesis in a culture *Methanococcus maripaludis* during exposure of a mixture of air and hydrogen gas.

Example 10—Maintained Methane Production by *Methanococcus maripaludis* in the Presence of Air FIG. 12 shows that methane production can continue even in the presence of air provided that hydrogen is present to maintain the ORP of the culture at productive levels. A bench bioreactor containing *Methanococcus maripaludis* was prepared as set forth in Example 2. The culture was exposed to a mixture of 4% air and 76% hydrogen at a flow rate of 100 cc/min and $CO_2$ at 25 cc/min for a period of 2.3 hours. The percentage of air was then increased to 8%, providing a mixture of 8% air and 72% hydrogen at a flow rate of 100 cc/min and $CO_2$ at 25 cc/min for a period of 1.7 hours. The percentage of air was then increased to 16%, providing a mixture of 16% air and 64% hydrogen at a flow rate of 100 cc/min and $CO_2$ at 25 cc/min for a period of 1.1 hours. Finally, the percentage of air was then increased to 32%, providing a mixture of 32% air and 58% hydrogen at a flow rate of 100 cc/min and $CO_2$ at 25 cc/min for a period of 0.6 hours. Methane production continues even in the presence of air provided that hydrogen is present to maintain the ORP of the culture at productive levels. Up to 4% air (0.8% oxygen) is tolerated without a persistent reduction in methane production. The efficiency of conversion of the input hydrogen to methane remains unaffected at 22-23% under the conditions of the experiment until the air concentration rises from 8% to 16% of the total gas mix.

Note that the gas mixtures produced by the culture under these conditions could be explosive, since the oxygen is not consumed by the organisms and appears in the effluent gas stream. A potentiostat culture system provides a method for maintaining the ORP of the culture during air exposure without introducing hydrogen or generating methane.

Example 11—Recovery from Carbon Monoxide Exposure by *Methanococcus maripaludis*

Figure 13:
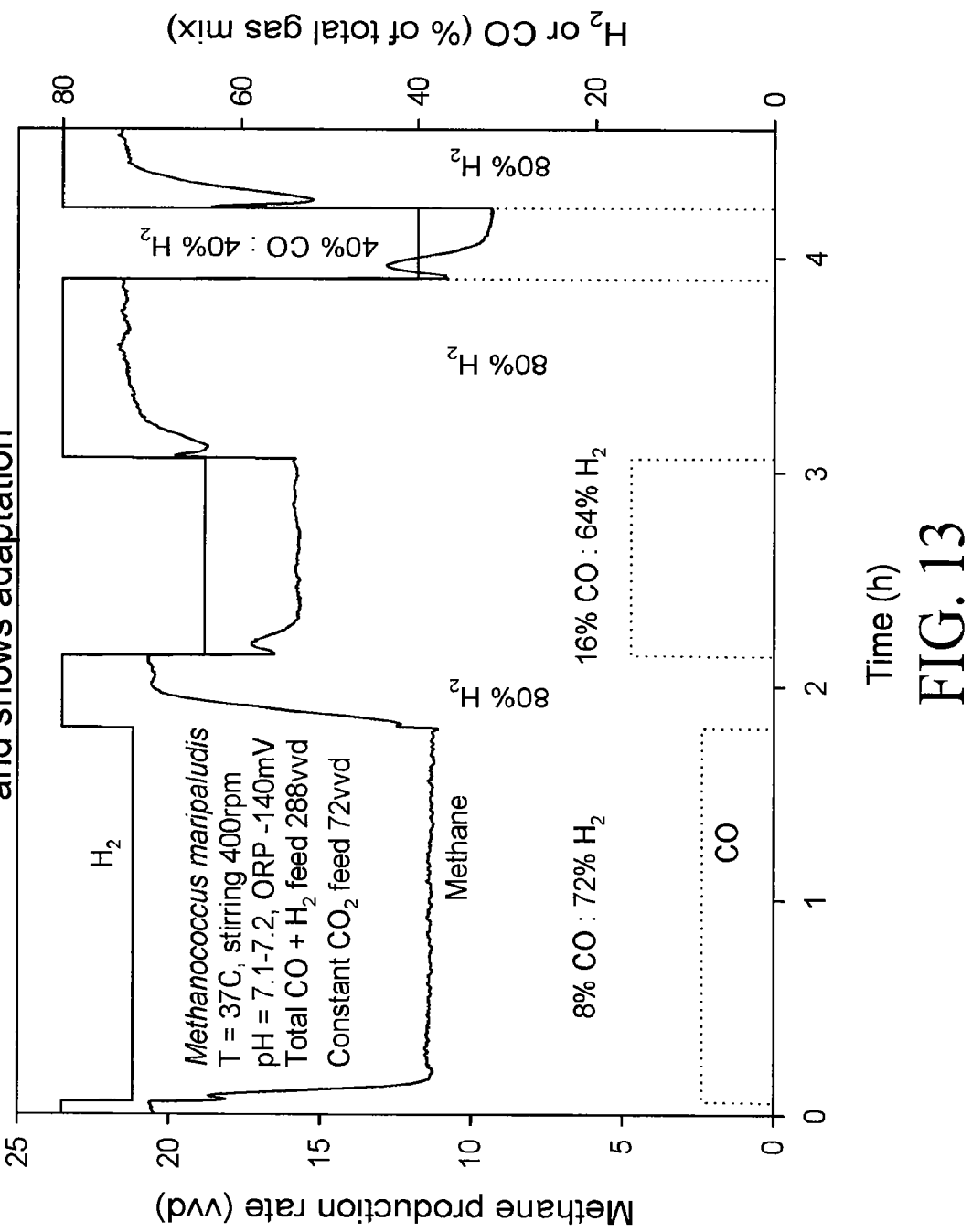
FIG. 13 is a chart showing the recovery of methanogenesis in a culture *Methanococcus maripaludis* during exposure of a mixture of carbon monoxide and hydrogen gas.

Carbon monoxide is another known inhibitor of enzymes involved in both hydrogen uptake and methanogenesis. CO is a potential contaminant of $CO_2$ and hydrogen streams derived from gasification of coal or biomass resources. The effect CO on methane formation by methanogen cultures was examined. FIG. 13 shows the recovery of the methanogenic activity of *Methanococcus maripaludis* after exposure to carbon monoxide. A bench bioreactor containing *Methanococcus maripaludis* was prepared as set forth in Example 2. In this experiment, the pH of the culture was maintained constant by keeping $CO_2$ at 20% of the gas mix and changing only the composition of the other 80% of the gas. The ORP of the culture remained relatively constant between −140 and −150 mV.

The culture was exposed to a mixture of 8% CO and 72% hydrogen at a flow rate of 100 cc/min and $CO_2$ at 25 cc/min for a period of 1.7 hours. Then the culture was restored to a flow of 80% hydrogen at a flow rate of 100 cc/min and $CO_2$ at 25 cc/min. Upon removal of the CO and restoration of 50% $H_2$, methanogenesis recovered completely within a 5 minutes (within the mixing time of the gas phase in the culture). This rapid recovery suggests that the primary effect of CO under these experimental conditions is as a reversible inhibitor of the methanogenesis process.

The culture was then exposed to a mixture of 16% CO and 64% hydrogen at a flow rate of 100 cc/min and $CO_2$ at 25 cc/min for a period of 1 hour. This higher exposure of CO showed only a 25% inhibition of methane formation rates. This suggests that the initial exposure caused an adaptation in the culture that reduced its sensitivity to CO inhibition. The culture was then restored to a flow of 80% hydrogen at a flow rate of 100 cc/min and $CO_2$ at 25 cc/min. Recovery of methanogenesis following CO removal was again immediate.

Finally, the culture was exposed to a mixture of 40% CO and 40% hydrogen at a flow rate of 100 cc/min and $CO_2$ at 25 cc/min for a period of 20 minutes. This CO exposure showed almost as much inhibition of the adapted process as occurred in the initial low level exposure of the un-adapted organisms. The culture was then restored to a flow of 80% hydrogen at a flow rate of 100 cc/min and $CO_2$ at 25 cc/min. Recovery from this level of CO was also immediate.

Figure 14:
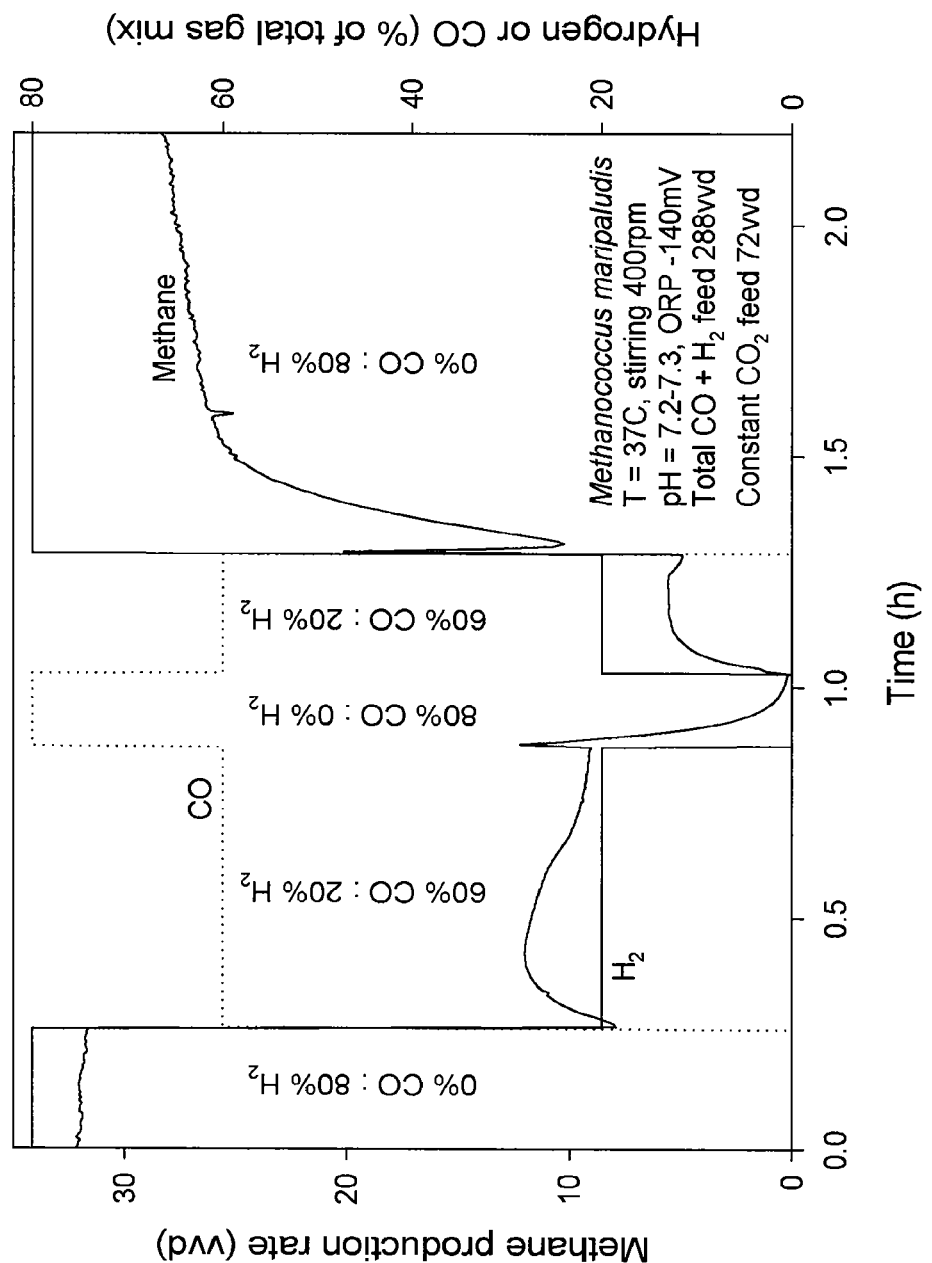
FIG. 14 is a chart showing the recovery of methanogenesis in a culture *Methanococcus maripaludis* during exposure of a mixture of carbon monoxide and hydrogen gas.

Another experiment was performed showing the effects of even higher concentration of CO on methanogenesis. A bench bioreactor containing *Methanococcus maripaludis* was prepared and maintained as set forth above. FIG. 14 shows that when the culture was given a doses of a mixture of 60% CO and 20% hydrogen at a flow rate of 100 cc/min and $CO_2$ at 25 cc/min, this led to a complete loss of methane formation in this species. Recovery from this level of CO has an immediate phase but full recovery requires several hours. These experiments show that methanogenesis achieved by methanogen cultures is tolerant to levels of CO likely to be found in industrial $CO_2$ streams derived from coal or biomass gasification, but that higher levels may be poorly tolerated.

Example 12—Efficiency of Methane Production from a Cascaded Bioreactor

A mathematical projection was performed to determine the projected efficiencies of methane production according to the methods of the present invention in a cascaded bioreactor system similar to what is depicted in FIG. 3. The performance of a methanogen culture in converting hydrogen and carbon dioxide to methane was modeled as a gas-phase continuously stirred tank reactor (CSTR) in which the gas is homogeneously mixed with a liquid phase in which the reaction occurs, catalyzed by the organisms. Under mass-transfer limited conditions, the reaction is first order in hydrogen with a rate that is governed by the gas-liquid transfer of hydrogen. The consumption of hydrogen by the organisms is sufficiently rapid to keep the dissolved concentration of hydrogen well below the saturating concentration. Under this model, the product of the first order rate constant, k, and the residence time of gas in the gas phase, $\tau$, govern the extent of the reaction of the hydrogen:

$$k\tau = \frac{X}{1-X},$$

where X is the fraction of hydrogen converted to methane. It is assumed that there is at least enough $CO_2$ present to consume all of the hydrogen in methane formation.

The extent of the reaction, X, is determined by the input flow of hydrogen gas, $F_o$ (in units of moles/time), the mass balance for the conversion to methane, and the first order rate constant, assuming constant volume, pressure and temperature:

$$F_o = \frac{kV_g P_g (1-X)}{RTX \left(\frac{5}{4} - X + D\right)}$$

where $V_g$ is the volume of the gas phase that is efficiently mixed with the liquid phase, $P_g$ is the operating pressure, R is the universal gas constant, T is the chamber temperature in ° K, and D is the total mole fraction in the gas phase of non-reactant gases, including any excess $CO_2$ as well as water vapor. As input reactant gas flow is increased, more product methane is produced, but at the expense of lower extent of reaction because of a lower retention time.

During the reaction, 4 volumes of hydrogen and 1 volume of carbon dioxide are consumed to produce 1 volume of methane. Hence, as the reaction proceeds, the flow of gas out of the chamber is less than the input flow. This strong reduction in flow during the reaction provides a uniquely valuable advantage to a system of cascaded reactors in which the exit gas from one reaction chamber becomes the inlet for a successive chamber. Under steady state conditions, the exit flow of hydrogen, F, is given by $F=F_o(1-X)$ in a given chamber. For a cascade of two identical chambers, the flow rate in the second chamber will be less than that in the first, and hence the retention time and the extent of conversion will be greater. The advantage of the cascade approach can be appreciated by comparing the extent of conversion in a single chamber of a fixed volume with the total extent of conversion of the same inlet gas flow by two cascaded chambers, each half the volume of the single chamber and with that of three cascaded chambers, each one third the volume of the single chamber, as shown in FIG. 15. For this illustration, the initial hydrogen:$CO_2$ ratio is 4:1.

TABLE 1

| | Conversion efficiency | |
|---|---|---|
| Single | Cascade | |
| Reactor | 2 reactor | 3 reactor |
| 0.3350 | 0.3626 | 0.3729 |
| 0.4562 | 0.5134 | 0.5368 |
| 0.5502 | 0.6389 | 0.6788 |
| 0.6222 | 0.7376 | 0.7927 |
| 0.6775 | 0.8110 | 0.8750 |
| 0.7204 | 0.8636 | 0.9280 |
| 0.7542 | 0.9004 | 0.9593 |
| 0.7813 | 0.9262 | 0.9770 |
| 0.8034 | 0.9443 | 0.9868 |
| 0.8369 | 0.9667 | 0.9954 |
| 0.9042 | 0.9928 | 0.9998 |

In this simulation, the input flow rate and the conversion rate constant were adjusted to give a range of extents of reaction in a single tank reactor. The extent of reaction, X, for this single reactor is listed in the first column of Table 1. The same initial flow rate was then fed to 2 or three cascaded reactors of ½ or ⅓ the volume of the single tank reactor, respectively, keeping the other reaction conditions constant.

The extent of reaction measured at the exit of the final reactor of the cascade is listed in the second and third columns of the table. The same data are also presented graphically in FIG. 15. Here, the final extent of reaction in the cascade, Xcascade, is divided by the extent of reaction of the equivalent total volume single reactor, Xsingle, and the ratio is plotted against Xsingle. Conditions near the peaks of these graphs would optimize the conversion gain of the cascade arrangement, while conditions to the right of the peaks would exploit the cascade for efficiently reducing the final residual unreacted hydrogen in the product gas stream.

This model assumes a homogeneous residence time for the gas. In practice, the bubbles suspended in the liquid act as independent mini-reactors for some period of time, a behavior that causes a dispersion of net conversion in different bubbles and in apparent residence times. This dispersion of residence times can be determined under operating conditions by injecting an inert gas tracer into the inlet gas stream and monitoring the time that it takes to exit. Depending on the exact shape of the residence time distribution, this phenomenon could degrade the performance of the single tank reactor. However, the use of cascading reactors sharpens the residence time distribution, which favors the cascaded reactor performance over that of a single reactor of the same total volume.

Example 13—Maintenance of a Methane Producing Culture of *Methanothermobacter thermoautotrophicus* in Stationary Phase

*Methanothermobacter thermoautotrophicus* (DSMZ 3590) was grown in a culture medium comprising: NaCl 10 mM, $NH_4Cl$ 120 mM, nitrilotriacetic acid (NTA) 1.2 mM, $MgCl_2 \cdot 7H_2O$ 1 mM, $KH_2PO_4$ 10 mM, $CoCl_2$ 2.5 $Na_2MoO_4$ 2.5 µM, $NiCl_2$ 5 µM, $FeSO_4 \cdot 7H_2O$ 0.2 mM, $Na_2ScO_3$ 1 µM, $Na_2WO_4$ 10 µM, at 60° C. in a 1.3 L BioFlo 110 fermenter vessel containing 700 ml medium and agitated at 1000 RPM until it reached stationary phase. During initial growth of the culture, sodium sulfide was added at a rate that maintained hydrogen sulfide in the output gas stream at ~10 ppm. The culture was sparged with a 4:1 $H_2:CO_2$ gas mixture at a total rate of 0.25 SLPM. In the stationary phase, a culture gassed at this rate produces 49 ml/min methane (101 vvd; 98% conversion of the input hydrogen). During methanogenesis, the culture produced two moles of metabolic water per mole of methane, which is a significant fraction of the medium volume. Medium, containing cells, was removed from the fermenter to keep the liquid volume constant. Medium components removed along with the liquid were replaced with concentrated stock solutions. During stationary phase, sulfide addition was necessary only for maintaining cell replacement and was maintained at a level below 1 ppm in the output gas stream.

Example 14—Recovery of Methane Production by *M. thermoautotrophicus* Following Exposure to Air A stationary phase culture of *M. thermoautotrophicus* 3590 producing methane at ~49 ml/min (101 vvd) from a 0.25 SLPM input gas stream of 4:1 $H_2:CO_2$ was exposed to air by replacing the hydrogen in the input gas mixture with air. The composition of the output gas was analyzed by mass spectrometry and the output rates of the various gases were computed in SLPM. As shown in FIG. 16, the output gas methane production declined immediately. After 1 hr, the air in the input gas was replaced with argon for 10 min and then with hydrogen, restoring the original 4:1 $H_2:CO_2$ gas mixture. After a lag of ~22 min, methane production recovered quickly, reaching 50% of the original production rate within 32 min and full 98% conversion efficiency by 57 min.

Example 15—Methane Production by a Stationary Phase Culture of *M. thermoautotrophicus* at Different Gassing Rates A stationary phase culture of *M. thermoautotrophicus* was grown as in Example 13, except with an initial hydrogen gassing rate in a 4:1 $H_2:CO_2$ mixture of 200 ml/min (450 vvd) and a liquid volume of 650 ml. This arrangement provides a 1:1 ratio of liquid culture to gaseous headspace and the agitation of 1000 RPM is adequate to maintain thorough mixing of the headspace with the liquid medium. The culture was then gassed at various rates with 4:1 $H_2:CO_2$ until the output gas composition stabilized. A pulse of argon gas was introduced into the gas feed stream as a tracer to measure the average residence time of the gas, τ. These data showed simple exponential decay of the gas tracer, indicating thorough mixing of the gas and liquid phases. The performance of the culture at each gassing rate is given in Table 2.

TABLE 2

| H2 in (vvd) | CH4 out (vvd) | X (fraction complete) | τ (s) |
|---|---|---|---|
| 450 | 111 | 0.987 | 299 |
| 900 | 215 | 0.955 | 98.8 |
| 1350 | 311 | 0.922 | 61.6 |
| 1800 | 399 | 0.886 | 47.8 |
| 2250 | 475 | 0.845 | 47 |
| 3150 | 595 | 0.755 | 35.9 |
| 4050 | 673 | 0.664 | 37.4 |
| 5400 | 758 | 0.562 | 33.3 |
| 6750 | 840 | 0.498 | ND |

A completely efficient catalyst (X=1.0) would yield 1012 vvd of methane from an input flow of 4050 vvd hydrogen. In practice, X at 4050 vvd hydrogen (1 atmosphere reactor pressure) is 0.664, corresponding to 673 vvd methane production in a single-pass continuously stirred tank reactor operating under the conditions specified. As projected in Example 12, a three-stage cascade reactor with the same total volume as the single reactor would operate with a final conversion efficiency improved to 0.86 and a corresponding increase in methane production to 860 vvd. A single reactor producing the same purity of product (same value of X) would produce only about 380 vvd methane from an input of 1700 vvd of hydrogen. If the volume of this same reactor operating at X=0.86 and 1700 vvd hydrogen input were divided into a three-tank cascade, it would produce ~425 vvd methane at X=0.99.

While the present invention has now been described and exemplified with some specificity, those skilled in the art will appreciate the various modifications, including variations, additions, and omissions that may be made in what has been described. It is to be understood that the invention is not limited in its application to the details of construction and the arrangements of the components set forth in the previous description or illustrated in the drawings. The invention is capable of other embodiments and of being practiced or being carried out in various ways. Accordingly, it is intended that these modifications also be encompassed by the present invention and that the scope of the present invention be limited solely by the broadest interpretation that lawfully can be accorded the appended claims.

Also, it is understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof. It also is understood that any numerical value recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between the lowest value and the highest value enumerated are to be considered to be expressly stated in this application.

The invention claimed is:

1. A method of converting carbon dioxide produced during an industrial process to methane comprising:
   a) contacting a culture comprising hydrogenotrophic methanogenic archaea with $H_2$ gas, $CO_2$ gas and an output gas from an industrial process in a bioreactor, wherein the output gas comprises $CO_2$ gas, carbon monoxide gas and between 0.1% to about 32% air by volume;
   b) supplying an amount of $H_2$ gas to maintain a redox potential in the bioreactor under −100 mV or less, wherein no additional constituent other than the $H_2$ gas is added to the bioreactor to maintain the redox potential in the bioreactor under −100 mV or less; and
   c) maintaining the redox potential of −100 mV or less, wherein the hydrogenotrophic methanogenic archaea continuously produces methane in the presence of oxygen.

2. The method of claim 1 wherein no sulfur is in the process other than sulfur in the culture medium.

3. The method of claim 1 wherein the hydrogenotrophic methanogenic archea comprises one or more species selected from the group consisting of *Methanobacterium alcaliphilum*, *Methanobacterium bryantii*, *Methanobacterium congolense*, *Methanobacterium defluvii*, *Methanobacterium espanolae*, *Methanobacterium formicicum*, *Methanobacterium ivanovii*, *Methanobacterium palustre*, *Methanobacterium thermaggregans*, *Methanobacterium uliginosum*, *Methanobrevibacter acididurans*, *Methanobrevibacter arboriphilicus*, *Methanobrevibacter gottschalkii*, *Methanobrevibacter olleyae*, *Methanobrevibacter ruminantium*, *Methanobrevibacter smithii*, *Methanobrevibacter woesei*, *Methanobrevibacter wolinii*, *Methanothermobacter marburgensis*, *Methanothermobacter thermautotrophicum*, *Methanothermobacter thermoflexus*, *Methanothermobacter thermophilus*, *Methanothermobacter wolfeii*, *Methanothermus sociabilis*, *Methanocorpusculum bavaricum*, *Methanocorpusculum parvum*, *Methanoculleus* chikuoensis, *Methanoculleus submarinus*, *Methanogenium frigidum*, *Methanogenium liminatans*, *Methanogenium marinum*, *Methanosarcina acetivorans*, *Methanosarcina barkeri*, *Methanosarcina mazei*, *Methanosarcina thermophila*, *Methanomicrobium mobile*, *Methanocaldococcus jannaschii*, *Methanococcus aeolicus*, *Methanococcus maripaludis*, *Methanococcus vannielii*, *Methanococcus voltaei*, *Methanothermococcus thermolithotrophicus*, *Methanopyrus kandleri*, *Methanothermobacter thermautotrophicus*, *Methanocaldococcus fervens*, *Methanocaldococcus indicus*, *Methanocaldococcus infernus*, and *Methanocaldococcus vulcanius*.

4. The method of claim 1 wherein the culture is a substantially pure culture of one hydrogenotrophic methanogenic archaea species.

5. The method of claim 1 wherein the industrial process is coal gasification, biomass gasification, or liquid fuel production by biomass fermentation.

6. The method of claim 1 wherein the conditions include a temperature of about 80° C. to about 100° C.

* * * * *